(12) United States Patent
Zucherman et al.

(10) Patent No.: US 8,109,972 B2
(45) Date of Patent: Feb. 7, 2012

(54) INTERSPINOUS PROCESS IMPLANT HAVING DEPLOYABLE WINGS AND METHOD OF IMPLANTATION

(75) Inventors: James F. Zucherman, San Francisco, CA (US); Ken Y. Hsu, San Francisco, CA (US); Henry A. Klyce, Piedmont, CA (US); Charles J. Winslow, Walnut Creek, CA (US); Scott A. Yerby, Montara, CA (US); John J. Flynn, Walnut Creek, CA (US); Steven T. Mitchell, Pleasant Hill, CA (US); John A. Markwart, Castro Valley, CA (US)

(73) Assignee: Kyphon SARL, Neuchatel (CH)

( * ) Notice: Subject to any disclaimer, the term of this patent is extended or adjusted under 35 U.S.C. 154(b) by 572 days.

(21) Appl. No.: 11/923,733

(22) Filed: Oct. 25, 2007

(65) Prior Publication Data
US 2008/0045958 A1    Feb. 21, 2008

Related U.S. Application Data

(63) Continuation of application No. 11/389,002, filed on Mar. 24, 2006.

(60) Provisional application No. 60/672,402, filed on Apr. 18, 2005.

(51) Int. Cl.
*A61B 17/70* (2006.01)

(52) U.S. Cl. ..................................... 606/249; 623/17.11

(58) Field of Classification Search .................. 606/426, 606/247, 248, 249, 250, 252, 63, 910, 279; 623/17.11, 17.16

See application file for complete search history.

(56) References Cited

U.S. PATENT DOCUMENTS

| | | | |
|---|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |

(Continued)

FOREIGN PATENT DOCUMENTS

DE        2821678 A1    11/1979

(Continued)

OTHER PUBLICATIONS

Benzel et al., "Posterior Cervical Interspinous Compression Wiring and Fusion for Mid to Low Cervical Spinal Injuries," J. Neurosurg., Jun. 1989, ppp. 893-899, vol. 70.

(Continued)

*Primary Examiner* — Pedro Philogene

(57) ABSTRACT

An embodiment of a system in accordance with the present invention can include an implant having a spacer with a thickness and a wing, wherein a first configuration of the wing has a first height substantially similar to the thickness and wherein the wing is adapted to be selectably arranged in a second configuration such that the wing has a second height greater than the first height. A periphery of the implant has a shape generally conformal with a shape of an inner surface of a cannula and a cross-sectional diameter smaller than an inner diameter of the cannula. The cannula is inserted such that a proximal end of the cannula is arranged between the adjacent spinous processes. The implant is then urged into position between the adjacent spinous processes by way of the cannula, and subsequently arranged in a second configuration to fix the implant in position.

9 Claims, 26 Drawing Sheets

U.S. PATENT DOCUMENTS

| | | | |
|---|---|---|---|
| 2,299,308 A | 10/1942 | Creighton | |
| 2,485,531 A | 10/1949 | Dzus et al. | |
| 2,607,370 A | 8/1952 | Anderson | |
| 2,677,369 A | 5/1954 | Knowles | |
| 2,685,877 A | 8/1954 | Dobelle | |
| 3,065,659 A | 11/1962 | Eriksson et al. | |
| 3,108,595 A * | 10/1963 | Overment | 604/105 |
| 3,426,364 A | 2/1969 | Lumb | |
| 3,648,691 A | 3/1972 | Lumb et al. | |
| 3,779,239 A | 12/1973 | Fischer et al. | |
| 4,011,602 A | 3/1977 | Rybicki et al. | |
| 4,237,875 A | 12/1980 | Termanini | |
| 4,257,409 A | 3/1981 | Bacal et al. | |
| 4,274,324 A | 6/1981 | Giannuzzi | |
| 4,289,123 A | 9/1981 | Dunn | |
| 4,401,112 A | 8/1983 | Rezaian | |
| 4,499,636 A | 2/1985 | Tanaka | |
| 4,519,100 A | 5/1985 | Wills et al. | |
| 4,553,273 A | 11/1985 | Wu | |
| 4,554,914 A | 11/1985 | Kapp et al. | |
| 4,573,454 A | 3/1986 | Hoffman | |
| 4,592,341 A | 6/1986 | Omagari et al. | |
| 4,599,086 A | 7/1986 | Doty | |
| 4,604,995 A | 8/1986 | Stephens et al. | |
| 4,611,582 A | 9/1986 | Duff | |
| 4,632,101 A | 12/1986 | Freedland | |
| 4,636,217 A | 1/1987 | Ogilvie et al. | |
| 4,646,998 A | 3/1987 | Pate | |
| 4,657,550 A | 4/1987 | Daher | |
| 4,662,808 A | 5/1987 | Camilleri | |
| 4,686,970 A | 8/1987 | Dove et al. | |
| 4,704,057 A | 11/1987 | McSherry | |
| 4,759,769 A | 7/1988 | Hedman et al. | |
| 4,787,378 A | 11/1988 | Sodhi | |
| 4,822,226 A | 4/1989 | Kennedy | |
| 4,827,918 A | 5/1989 | Olerud | |
| 4,834,600 A | 5/1989 | Lemke | |
| 4,863,476 A | 9/1989 | Shepperd | |
| 4,886,405 A | 12/1989 | Blomberg | |
| 4,892,545 A | 1/1990 | Day et al. | |
| 4,913,144 A | 4/1990 | Del Medico | |
| 4,931,055 A | 6/1990 | Bumpus et al. | |
| 4,932,975 A | 6/1990 | Main et al. | |
| 4,969,887 A | 11/1990 | Sodhi | |
| 5,000,166 A | 3/1991 | Karpf | |
| 5,011,484 A | 4/1991 | Breard | |
| 5,047,055 A | 9/1991 | Bao et al. | |
| 5,059,193 A | 10/1991 | Kuslich | |
| 5,092,866 A | 3/1992 | Breard et al. | |
| 5,098,433 A | 3/1992 | Freedland | |
| 5,171,278 A | 12/1992 | Pisharodi | |
| 5,201,734 A | 4/1993 | Cozad et al. | |
| 5,267,999 A | 12/1993 | Olerud | |
| 5,290,312 A | 3/1994 | Kojimoto et al. | |
| 5,306,275 A | 4/1994 | Bryan | |
| 5,306,310 A | 4/1994 | Siebels | |
| 5,312,405 A | 5/1994 | Korotko et al. | |
| 5,360,430 A | 11/1994 | Lin | |
| 5,366,455 A | 11/1994 | Dove | |
| 5,370,697 A | 12/1994 | Baumgartner | |
| 5,390,683 A * | 2/1995 | Pisharodi | 128/898 |
| 5,395,370 A | 3/1995 | Muller et al. | |
| 5,401,269 A | 3/1995 | Buttner-Janz et al. | |
| 5,403,316 A | 4/1995 | Ashman | |
| 5,415,661 A | 5/1995 | Holmes | |
| 5,437,672 A | 8/1995 | Alleyne | |
| 5,437,674 A | 8/1995 | Worcel et al. | |
| 5,439,463 A | 8/1995 | Lin | |
| 5,454,365 A * | 10/1995 | Bonutti | 600/204 |
| 5,454,812 A | 10/1995 | Lin | |
| 5,458,641 A | 10/1995 | Ramirez Jimenez | |
| 5,480,442 A | 1/1996 | Bertagnoli | |
| 5,496,318 A | 3/1996 | Howland et al. | |
| 5,518,498 A | 5/1996 | Lindenberg et al. | |
| 5,554,191 A | 9/1996 | Lahille et al. | |
| 5,562,662 A | 10/1996 | Brumfield et al. | |
| 5,562,735 A | 10/1996 | Margulies | |
| 5,571,192 A | 11/1996 | Schonhoffer | |
| 5,609,634 A | 3/1997 | Voydeville | |
| 5,609,635 A | 3/1997 | Michelson | |
| 5,628,756 A | 5/1997 | Barker, Jr. et al. | |
| 5,630,816 A | 5/1997 | Kambin | |
| 5,645,599 A | 7/1997 | Samani | |
| 5,653,762 A | 8/1997 | Pisharodi | |
| 5,653,763 A | 8/1997 | Errico et al. | |
| 5,658,335 A | 8/1997 | Allen | |
| 5,665,122 A | 9/1997 | Kambin | |
| 5,674,295 A | 10/1997 | Ray et al. | |
| 5,676,702 A | 10/1997 | Ratron | |
| 5,685,826 A | 11/1997 | Bonutti | |
| 5,690,649 A | 11/1997 | Li | |
| 5,693,100 A | 12/1997 | Pisharodi | |
| 5,702,395 A | 12/1997 | Hopf | |
| 5,702,452 A | 12/1997 | Argenson et al. | |
| 5,702,455 A | 12/1997 | Saggar | |
| 5,707,390 A * | 1/1998 | Bonutti | 606/204 |
| 5,716,416 A | 2/1998 | Lin | |
| 5,723,013 A | 3/1998 | Jeanson et al. | |
| 5,725,341 A | 3/1998 | Hofmeister | |
| 5,746,762 A | 5/1998 | Bass | |
| 5,755,797 A | 5/1998 | Baumgartner | |
| 5,800,547 A | 9/1998 | Schafer et al. | |
| 5,810,815 A | 9/1998 | Morales | |
| 5,836,948 A | 11/1998 | Zucherman et al. | |
| 5,849,004 A | 12/1998 | Bramlet | |
| 5,860,977 A | 1/1999 | Zucherman et al. | |
| 5,888,196 A | 3/1999 | Bonutti | |
| 5,941,881 A | 8/1999 | Barnes | |
| 5,976,186 A | 11/1999 | Bao et al. | |
| 5,980,523 A | 11/1999 | Jackson | |
| 6,022,376 A | 2/2000 | Assell et al. | |
| 6,048,342 A | 4/2000 | Zucherman et al. | |
| 6,068,630 A | 5/2000 | Zucherman et al. | |
| 6,126,689 A | 10/2000 | Brett | |
| 6,126,691 A | 10/2000 | Kasra et al. | |
| 6,127,597 A | 10/2000 | Beyar et al. | |
| 6,132,464 A | 10/2000 | Martin | |
| 6,190,413 B1 | 2/2001 | Sutcliffe | |
| 6,190,414 B1 | 2/2001 | Young | |
| 6,214,050 B1 | 4/2001 | Huene | |
| 6,293,949 B1 | 9/2001 | Justis et al. | |
| 6,336,930 B1 | 1/2002 | Stalcup et al. | |
| 6,348,053 B1 | 2/2002 | Cachia | |
| 6,352,537 B1 | 3/2002 | Strnad | |
| 6,364,883 B1 | 4/2002 | Santilli | |
| 6,371,987 B1 | 4/2002 | Weiland et al. | |
| 6,375,682 B1 | 4/2002 | Fleischmann et al. | |
| 6,402,750 B1 | 6/2002 | Atkinson et al. | |
| 6,402,751 B1 | 6/2002 | Hoeck et al. | |
| 6,419,704 B1 | 7/2002 | Ferree | |
| 6,440,169 B1 | 8/2002 | Elberg et al. | |
| 6,447,513 B1 | 9/2002 | Griggs | |
| 6,451,019 B1 | 9/2002 | Zucherman et al. | |
| 6,500,178 B2 | 12/2002 | Zucherman et al. | |
| 6,514,256 B2 | 2/2003 | Zucherman et al. | |
| 6,520,991 B2 | 2/2003 | Huene | |
| 6,554,833 B2 * | 4/2003 | Levy et al. | 606/63 |
| 6,582,433 B2 | 6/2003 | Yun | |
| 6,582,467 B1 | 6/2003 | Teitelbaum et al. | |
| 6,592,585 B2 | 7/2003 | Choi et al. | |
| 6,626,944 B1 | 9/2003 | Taylor | |
| 6,645,207 B2 | 11/2003 | Dixon et al. | |
| 6,685,742 B1 | 2/2004 | Jackson | |
| 6,695,842 B2 | 2/2004 | Zucherman et al. | |
| 6,709,435 B2 | 3/2004 | Lin | |
| 6,723,126 B1 | 4/2004 | Berry | |
| 6,730,126 B2 | 5/2004 | Boehm, Jr. et al. | |
| 6,733,534 B2 | 5/2004 | Sherman | |
| 6,736,818 B2 | 5/2004 | Perren et al. | |
| 6,743,257 B2 | 6/2004 | Castro | |
| 6,758,863 B2 | 7/2004 | Estes et al. | |
| 6,761,720 B1 | 7/2004 | Senegas | |
| 6,770,096 B2 | 8/2004 | Bolger et al. | |
| 6,783,530 B1 | 8/2004 | Levy | |
| 6,835,205 B2 | 12/2004 | Atkinson et al. | |
| 6,905,512 B2 | 6/2005 | Paes et al. | |
| 6,946,000 B2 | 9/2005 | Senegas et al. | |

| | | |
|---|---|---|
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,081,120 B2 | 7/2006 | Li et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,621,950 B1 | 11/2009 | Globerman et al. |
| 2001/0016743 A1 | 8/2001 | Zucherman et al. |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0010312 A1 | 1/2004 | Enayati |
| 2004/0010316 A1 | 1/2004 | William et al. |
| 2004/0087947 A1 | 5/2004 | Lim et al. |
| 2004/0097931 A1 | 5/2004 | Mitchell |
| 2004/0133204 A1 | 7/2004 | Davies |
| 2004/0133280 A1 | 7/2004 | Trieu |
| 2004/0167625 A1 | 8/2004 | Beyar et al. |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0049708 A1 | 3/2005 | Atkinson et al. |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0032790 A1 | 2/2007 | Aschmann et al. |
| 2007/0043362 A1 | 2/2007 | Malandain et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0215094 A1 | 9/2008 | Taylor |
| 2008/0221685 A9 | 9/2008 | Altarac et al. |
| 2008/0234824 A1 | 9/2008 | Youssef et al. |
| 2008/0262617 A1 | 10/2008 | Froehlich et al. |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105766 A1 | 4/2009 | Thompson et al. |
| 2009/0105773 A1 | 4/2009 | Lange et al. |
| 2009/0234389 A1 | 9/2009 | Chuang et al. |
| 2009/0270918 A1 | 10/2009 | Attia et al. |
| 2010/0121379 A1 | 5/2010 | Edmond |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084768 A2 | 10/2004 |
| WO | 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007/052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, Dispositif Intervertébral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de Ia Stabilité Rachidienne," Tiré de Ia Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrates Lombaires, Gastambide, ed., 1995, pp. 122-132, Expansion Scientifique Française, Paris, France.

Senegas, "La Ligamentoplastie Inter Vertébrate Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

* cited by examiner

INTERSPINOUS PROCESS IMPLANT HAVING DEPLOYABLE WINGS AND METHOD OF IMPLANTATION

CROSS-REFERENCE TO RELATED APPLICATIONS

This application is a continuation of U.S. patent application Ser. No. 11/389,002, entitled "Interspinous Process Implant Having Deployable Wings and Method of Implantation," filed Mar. 24, 2006, which claims priority to U.S. Provisional Patent Application No. 60/672,402, entitled "Interspinous Process Implant Having Deployable Wings and Method of Implantation," filed Apr. 18, 2005; each of which is incorporated herein by reference in its entirety.

This U.S. Patent Application incorporates by reference all of the following co-pending applications and issued patents:

U.S. patent application Ser. No. 10/850,267 entitled "Distractible Interspinous Process Implant and Method of Implantation," by Zucherman et al., filed May 20, 2004;

U.S. Patent Application No. 60/612,465 entitled "Interspinous Process Implant Including a Binder and Method of Implantation," by Zucherman et al., filed Sep. 20, 2004;

U.S. Pat. No. 6,419,676, entitled "Spine Distraction Implant and Method," issued Jul. 16, 2002 to Zucherman, et al.;

U.S. Pat. No. 6,451,019, entitled "Supplemental Spine Fixation Device and Method," issued Sep. 17, 2002 to Zucherman, et al.;

U.S. Pat. No. 6,582,433, entitled "Spine Fixation Device and Method," issued Jun. 24, 2003 to Yun;

U.S. Pat. No. 6,652,527, entitled "Supplemental Spine Fixation Device and Method," issued Nov. 25, 2003 to Zucherman, et al.;

U.S. Pat. No. 6,695,842, entitled "Interspinous Process Distraction System and Method with Positionable Wing and Method," issued Feb. 24, 2004 to Zucherman, et al.;

U.S. Pat. No. 6,699,246, entitled "Spine Distraction Implant," issued Mar. 2, 2004 to Zucherman, et al.; and U.S. Pat. No. 6,712,819, entitled "Mating Insertion Instruments for Spinal Implants and Methods of Use," issued Mar. 30, 2004 to Zucherman, et al.

BACKGROUND

This invention relates to interspinous process implants. The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk and arms to the pelvis and legs, (2) complex physiological motion between these parts, and (3) protection of the spinal cord and the nerve roots.

As the present society ages, it is anticipated that there will be an increase in adverse spinal conditions which are characteristic of older people. By way of example only, with aging comes an increase in spinal stenosis (including, but not limited to, central canal and lateral stenosis), and facet arthropathy. Spinal stenosis results in a reduction foraminal area (i.e., the available space for the passage of nerves and blood vessels) which compresses the cervical nerve roots and causes radicular pain. Humpreys, S. C. et al., Flexion and traction effect on C5-C6 foraminal space, Arch. Phys. Med. Rehabil., vol. 79 at 1105 (September 1998). Another symptom of spinal stenosis is myelopathy, which results in neck pain and muscle weakness. Id. Extension and ipsilateral rotation of the neck further reduces the foraminal area and contributes to pain, nerve root compression and neural injury. Id.; Yoo, J. U. et al., Effect of cervical spine motion on the neuroforaminal dimensions of human cervical spine, Spine, vol. 17 at 1131 (Nov. 10, 1992). In contrast, neck flexion increases the foraminal area. Humpreys, S. C. et al., at 1105. Pain associated with stenosis can be relieved by medication and/or surgery. It is desirable to eliminate the need for major surgery for all individuals, and in particular, for the elderly.

Accordingly, a need exists to develop spine implants that alleviate pain caused by spinal stenosis and other such conditions caused by damage to, or degeneration of, the cervical spine. Such implants would distract, or increase the space between, the vertebrae to increase the foraminal area and reduce pressure on the nerves and blood vessels of the cervical spine.

A further need exists for development of a minimally invasive surgical implantation method for cervical spine implants that preserves the physiology of the spine.

Further, a need exists for an implant that accommodates the distinct anatomical structures of the spine, minimizes further trauma to the spine, and obviates the need for invasive methods of surgical implantation. Additionally, a need exists to address adverse spinal conditions that are exacerbated by spinal extension.

BRIEF DESCRIPTION OF THE DRAWINGS

Further details of embodiments of the present invention are explained with the help of the attached drawings in which.

DETAILED DESCRIPTION

Interspinous Implants

Figure 1:
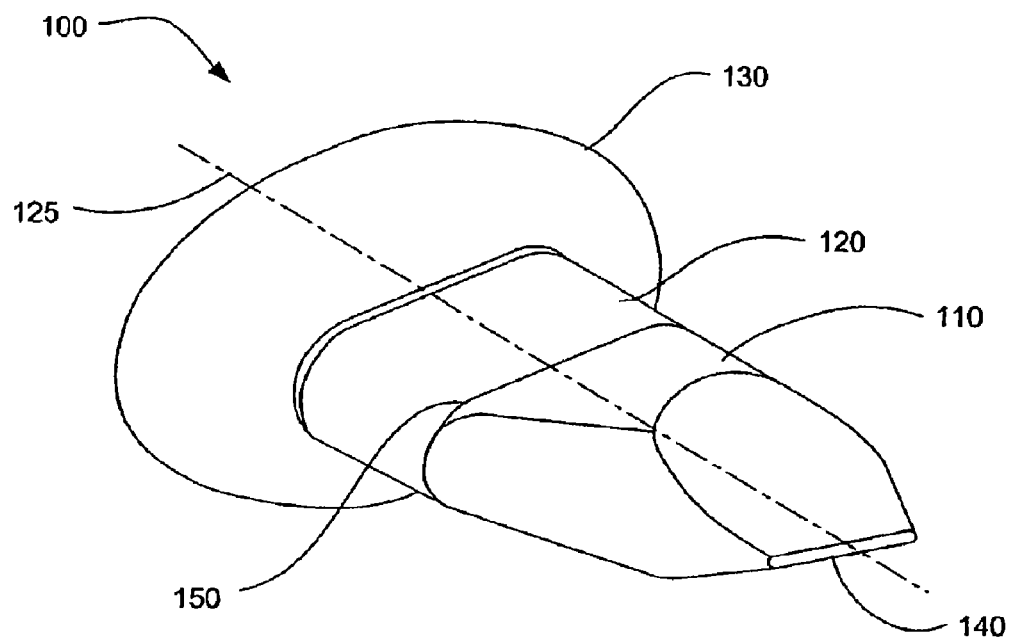
FIG. 1 is a perspective view of an embodiment of an implant in accordance with the present invention having a spacer, a distraction guide, and a wing with an elliptical cross-section.
Figure 2:
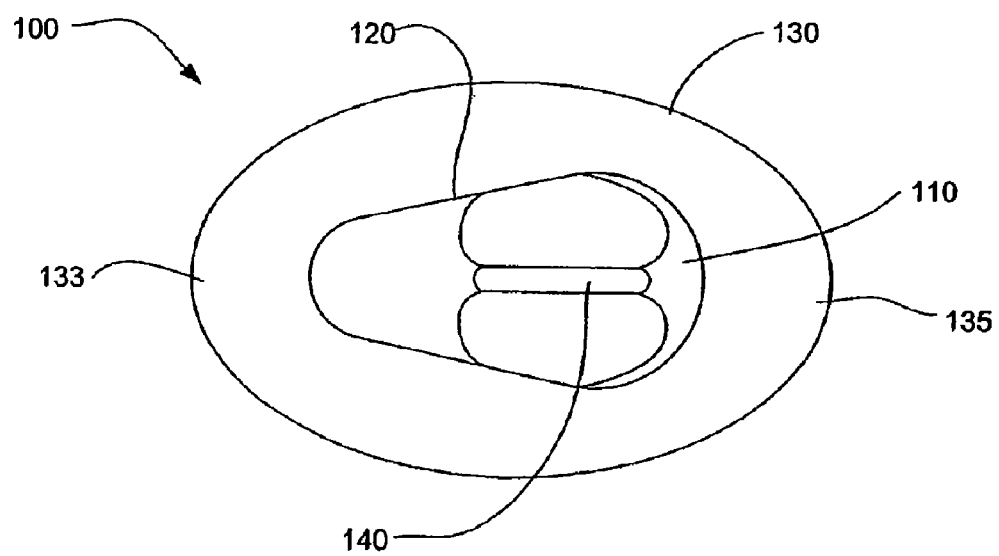
FIG. 2 is an end view of the implant of FIG. 1.

FIGS. 1 and 2 illustrate an implant 100 in accordance with an embodiment of the present invention. The implant 100 comprises a wing 130, a spacer 120, and a lead-in tissue expander (also referred to herein as a distraction guide) 110. The distraction guide 110 in this particular embodiment is wedge-shaped, i.e., the implant has an expanding cross-section from a distal end of the implant 102 to a region 104 where the guide 110 joins with the spacer 120 (referencing for the figures is based on the point of insertion of the implant between spinous processes). As such, the distraction guide functions to initiate distraction of the soft tissue and the spinous processes when the implant 100 is surgically inserted between the spinous processes. It is to be understood that the distraction guide 110 can be pointed and the like, in order to facilitate insertion of the implant 100 between the spinous processes of adjacent cervical vertebrae. It is advantageous that the insertion technique disturb as little of the bone and surrounding tissue or ligaments as possible in order to reduce trauma to the site and promote early healing, and prevent destabilization of the normal anatomy. In the embodiment of FIGS. 1 and 2, there is no requirement to remove any of the bone of the spinous processes and no requirement to sever or remove from the body ligaments and tissues immediately associated with the spinous processes. For example, it is unnecessary to sever the ligamentum nuchae (supraspinous ligament), which partially cushions the spinous processes of the upper cervical vertebrae.

Figure 3:
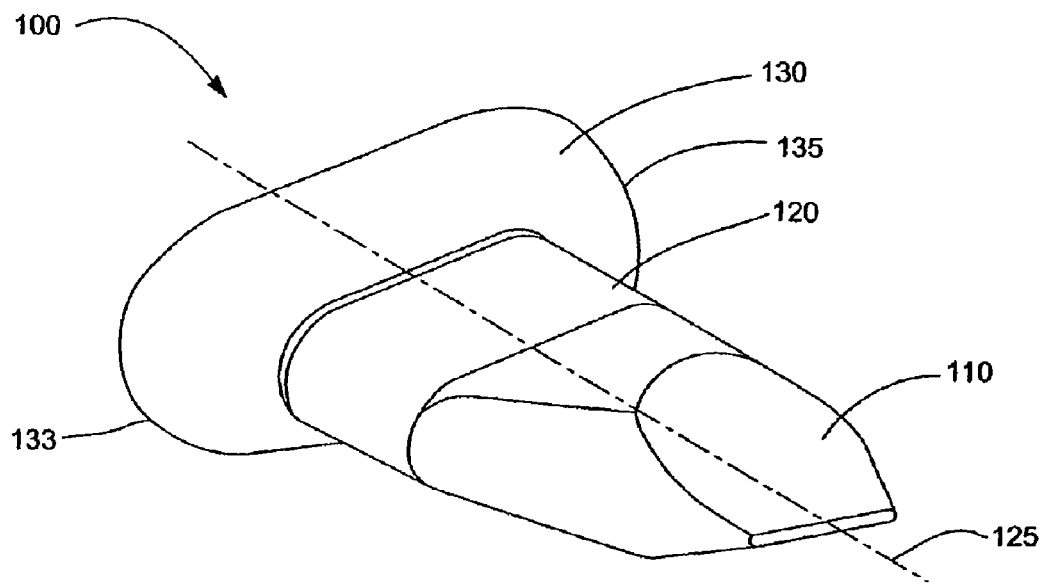
FIG. 3 is a perspective view of another embodiment of an implant in accordance with the present invention having a wing with a teardrop-shaped cross-section.

As can be seen in FIGS. 1-3, the spacer 120 can be teardrop-shaped in cross-section perpendicular to a longitudinal axis 125 of the implant 100. In this way, the shape of the spacer 120 can roughly conform to a wedge-shaped space, or a portion of the space, between adjacent spinous processes within which the implant 100 is to be positioned. In other embodiments, the spacer 120, can have alternative shapes such as circular, wedge, elliptical, ovoid, football-shaped, and rectangular-shaped with rounded corners and other shapes, and be within the spirit and scope of the invention. The shape of the spacer 120 can be selected for a particular patient so that the physician can position the implant 100 as close as possible to the anterior portion of the surface of the spinous process. The shape selected for the spacer 120 can affect the contact surface area of the implant 100 and the spinous processes that are to be subject to distraction. Increasing the contact surface area between the implant 100 and the spinous processes can distribute the force and load between the spinous frame and the implant 100.

As can be seen in FIGS. 1 and 2, the wing 130 in an embodiment can be elliptically shaped in cross-section perpendicular to the longitudinal axis 125. The dimensions of the wing 130 can be larger than that of the spacer 120, particularly along the axis of the spine, and can limit or block lateral displacement of the implant 100 in the direction of insertion along the longitudinal axis 125. As illustrated in the embodiment of FIG. 3, the wing 130 can alternatively have other cross-sectional shapes, such as teardrop, wedge, circular, ovoid, football-shaped, and rectangular-shaped with rounded corners and other shapes, and be within the spirit and scope of the invention. The wing 130 has an anterior portion 138 and a posterior portion 136.

In other embodiments, the implant 100 can include two wings, with a second wing 160 (shown in FIG. 4) separate from the distraction guide 110, spacer 120 and first wing 130. The second wing 160 can be connected to the distal end of the spacer 120. The second wing 160, similar to the first wing 130, can limit or block lateral displacement of the implant 100, however displacement is limited or blocked in the direction along the longitudinal axis 125 opposite insertion. When both the first wing 130 and the second wing 160 are connected with the implant 100 and the implant 100 is positioned between adjacent spinous processes, a portion of the spinous processes can be sandwiched between the first wing 130 and the second wing 160, limiting any displacement along the longitudinal axis 125.

Figure 4:
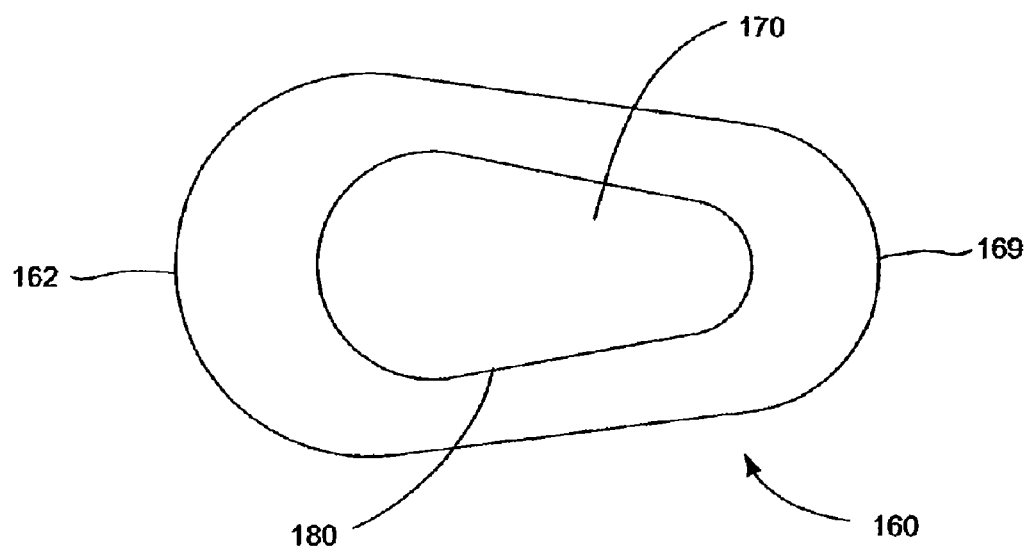
FIG. 4 is an end view of a second wing for use with the implant of FIG. 3.

As can be seen in FIG. 4, the second wing 160 can be teardrop-shaped in cross-section. The wider end 166 of the second wing 160 is the posterior end and the narrower end 168 of the second wing 160 is the anterior end. Unlike the first wing 130, however, an opening 164 is defined within the second wing 160, the opening 164 being at least partially circumscribed by a lip 162 that allows the second wing 160 to pass over the distraction guide 110 to meet and connect with the spacer 120. The second wing 160 can be secured to the spacer 120 once the second wing 160 is properly positioned. The second wing 160 can be connected with the implant after the implant 100 is positioned between the spinous processes.

It is to be understood that the implant can be made in two pieces. The first piece can include the first wing 130, the spacer 120, and the distraction guide 110. The second piece can include the second wing 160. Each piece can be manufactured using technique known in the art (e.g., machining, molding, extrusion). Each piece, as will be more fully discussed below, can be made of a material that is bio-compatible with the body of the patient. An implant can be formed with multiple pieces and with the pieces appropriately joined together, or alternatively, an implant can be formed as one piece or joined together as one piece.

Figure 5:
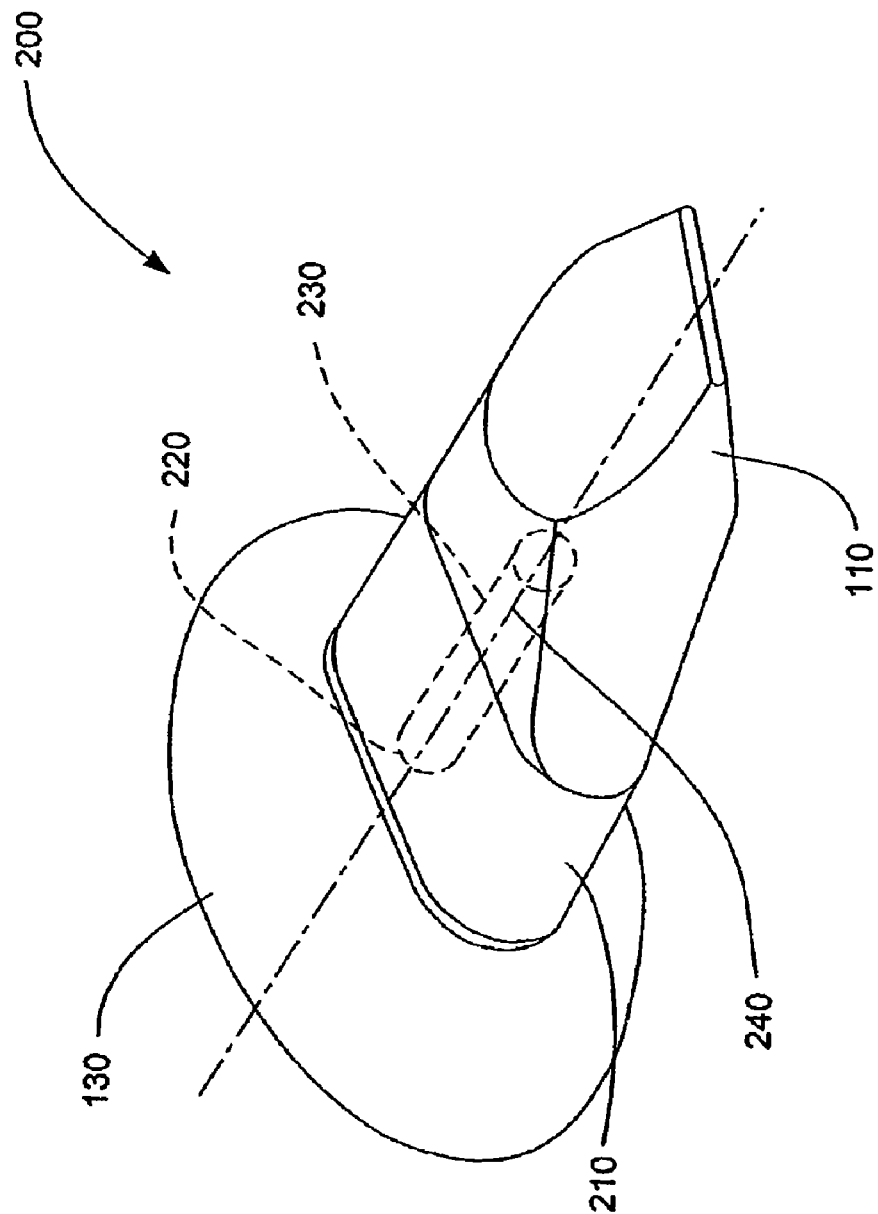
FIG. 5 is a perspective view of an embodiment of an implant in accordance with the present invention having a rotatable spacer and a wing with an elliptical cross-section.
Figure 6:
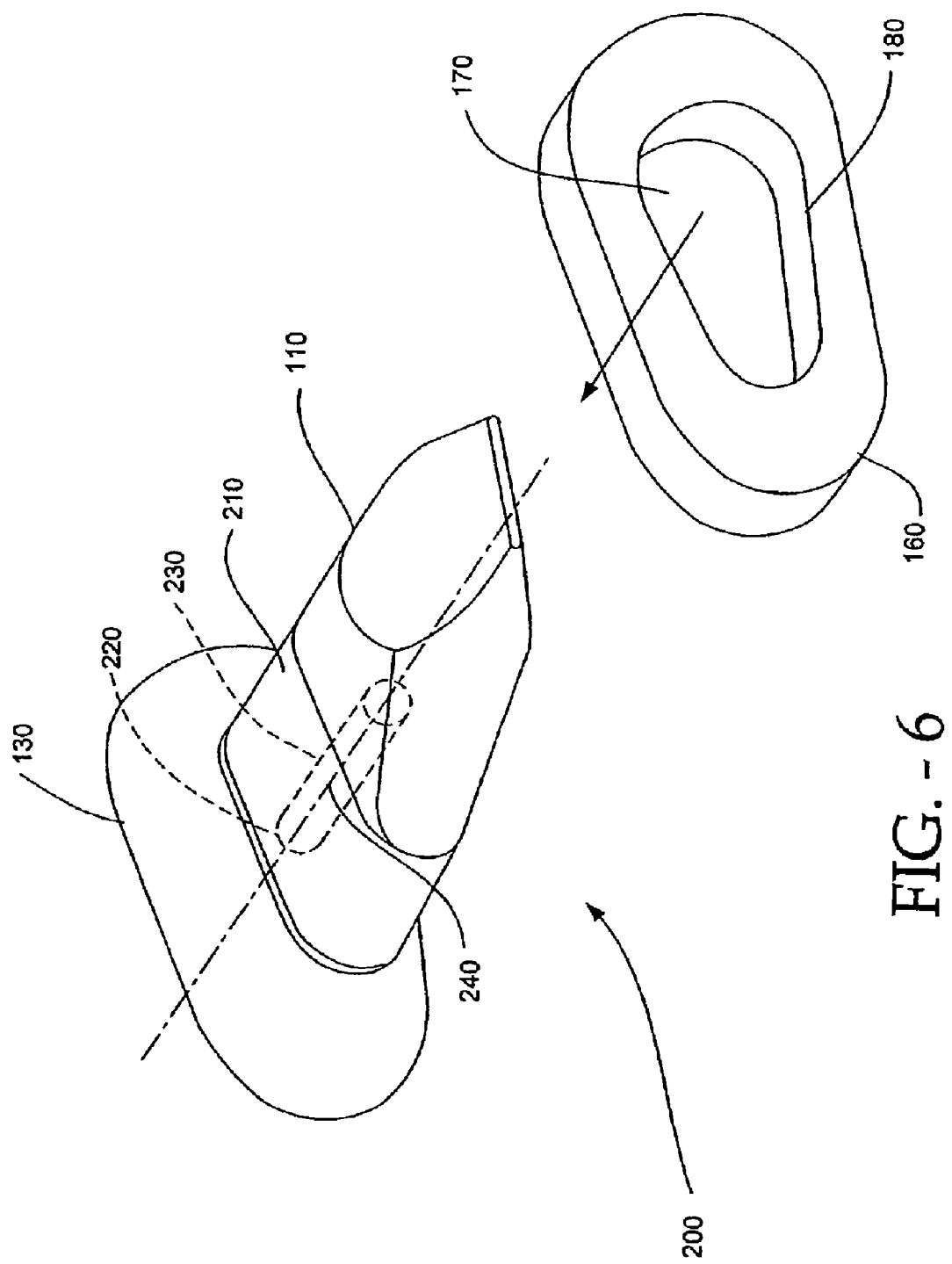
FIG. 6 is a perspective view of an embodiment of an implant in accordance with the present invention having a rotatable spacer with two wings that are teardrop-shaped in cross-section.
Figure 7:
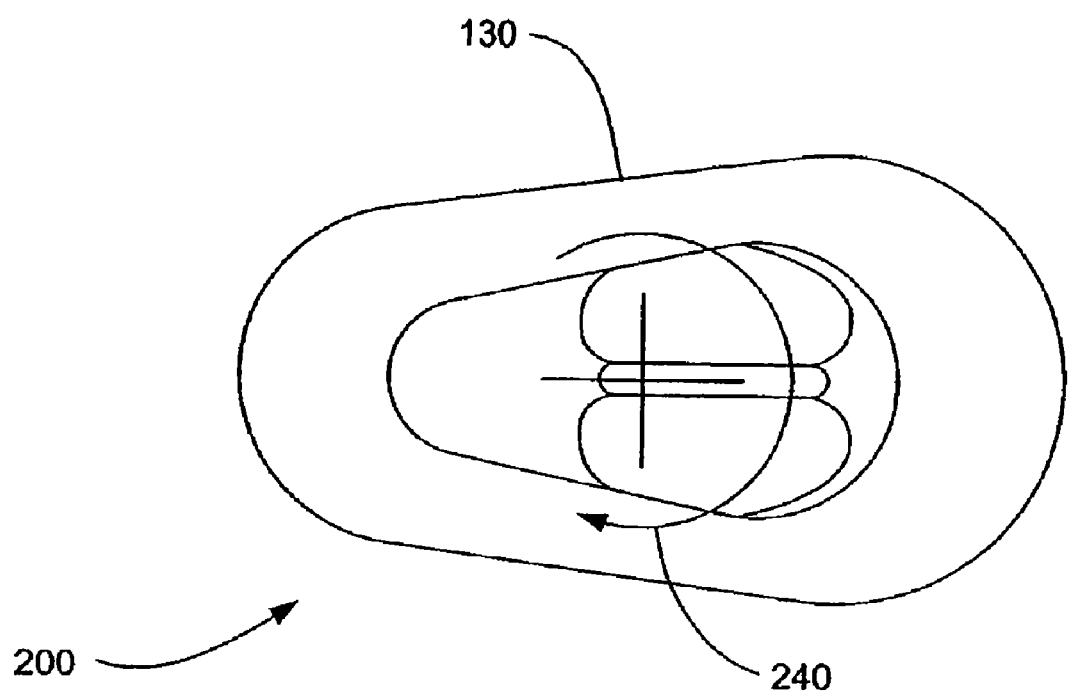
FIG. 7 depicts the axis of rotation of the implant of FIG. 6 as seen from an end view.

Further embodiments of implants in accordance with the present invention are depicted in FIGS. 5-7. In such embodiments, the spacer 220 can be rotatable about the longitudinal axis 225 relative to the first wing 130, or relative to the first wing 130 and a second wing 160 where two wings are used. The spacer 220 can be rotatable or fixed relative to the distraction guide 110. Where the spacer 220 is rotatable relative to the distraction guide 110, the spacer 220 can include a bore 222 running the length of the longitudinal axis 225, and a shaft 224 inserted through the bore 222 and connecting the distraction guide 110 with the first wing 130. It can be advantageous to position any of the implants taught herein as close as possible to the vertebral bodies. The rotatable spacer 220 can rotate to conform to or settle between adjacent spinous processes as the implant 200 is inserted and positioned during implantation, so that on average the contact surface area between the spacer 220 and the spinous processes can be increased over the contact surface area between a fixed spacer 120 and the spinous processes. Thus, the rotatable spacer 220 can improve the positioning of the spacer 220 independent of the wings 130,160 relative to the spinous processes. The embodiment of FIG. 6 includes a teardrop-shaped first wing 130, and a teardrop-shaped second wing 160, similar to the second wing 160 depicted in the embodiment of FIG. 3. As discussed below, the shape of the wings 130,160 in FIGS. 3 and 6 is such that the implants 100,200 accommodate the twisting of the cervical spine along its axis, for example, as the head of a patient turns from side-to-side.

Figure 8:
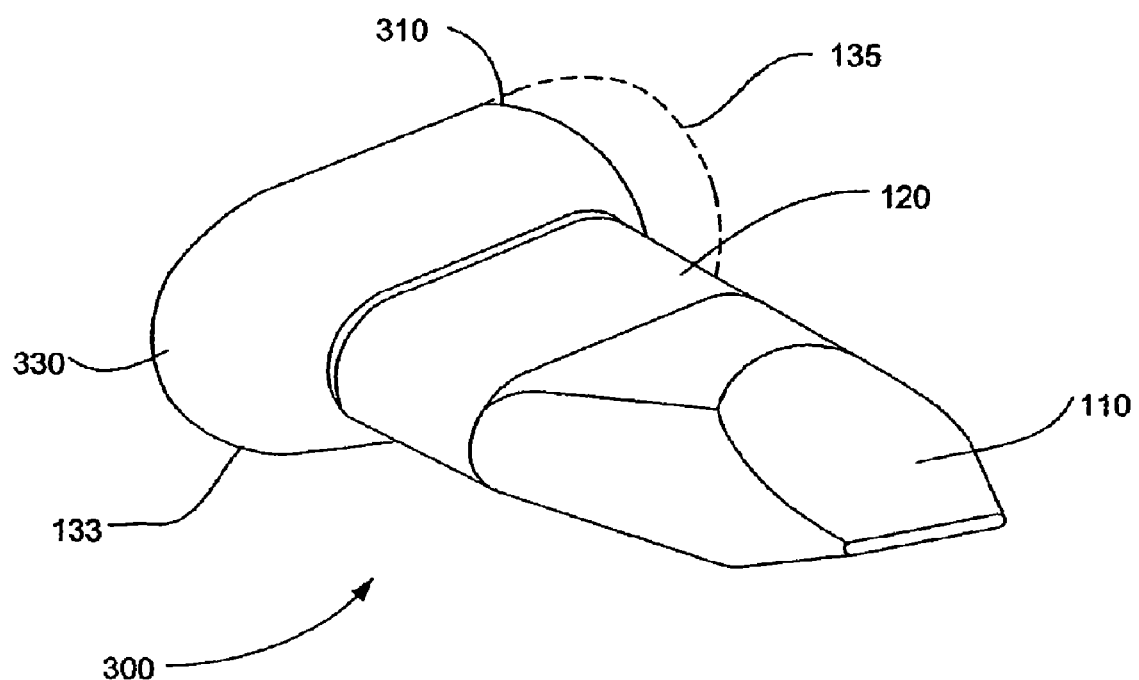
FIG. 8 is a perspective view of an embodiment of an implant in accordance with the present invention having a wing that is truncated at a posterior end.
Figure 9A:
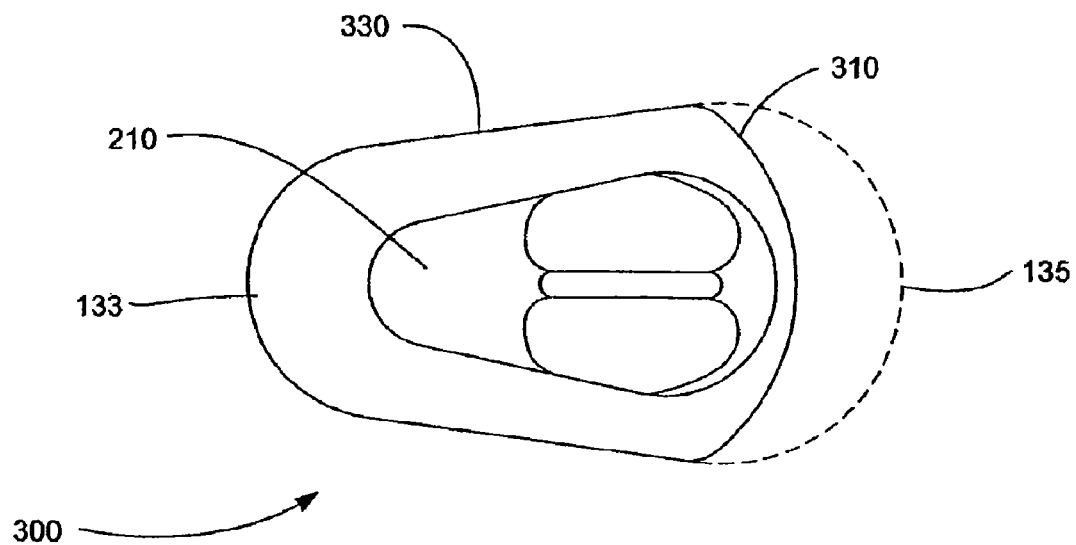
FIG. 9A is an end view of the implant of FIG. 8.
Figure 9B:
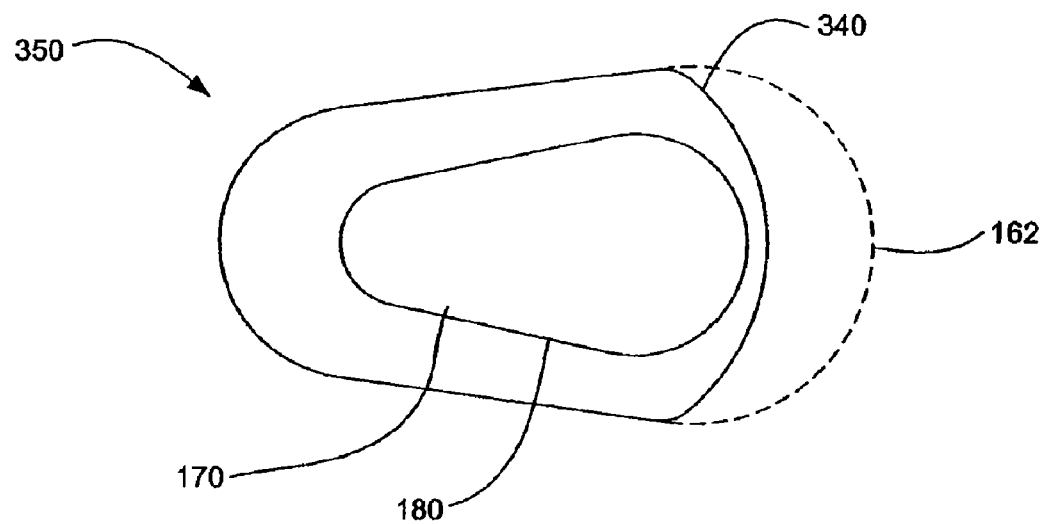
FIG. 9B is a truncated second wing for use with the implant of FIG. 9A.

FIG. 8 is a perspective view and FIG. 9A is an end view of still another embodiment of an implant in accordance with the present invention, wherein the posterior portion 336 of the teardrop-shaped first wing 330 is truncated, making the first wing 330 more ovoid in shape. In this configuration, the anterior portion 138 of the first wing 330 can be longer than the truncated posterior end 336 of the first wing 330. As in previous embodiments, the spacer 120 can alternatively be a rotatable spacer rather than a fixed spacer. FIG. 9B illustrates a second wing 360 for use with such implants 300, the second wing 360 having a truncated posterior end 366. Truncation of the posterior ends 336,366 of the first and second wings 330,360 can reduce the possibility of interference of implants 300 having such first and second wings 330,360 positioned between spinous processes of adjacent pairs of cervical vertebrae, e.g., implants between cervical vertebrae five and six, and between cervical vertebrae six and seven. During rotation of the neck, the spinous process move past each other in a scissor-like motion. Each cervical vertebra can rotate relative to the next adjacent cervical vertebra in the general range of about 6°-12°. In addition, about 50 percent of the rotational movement of the neck is accomplished by the top two neck vertebrae. Thus, such embodiments can accommodate neck rotation without adjacent embodiments interfering with each other.

Figure 10:
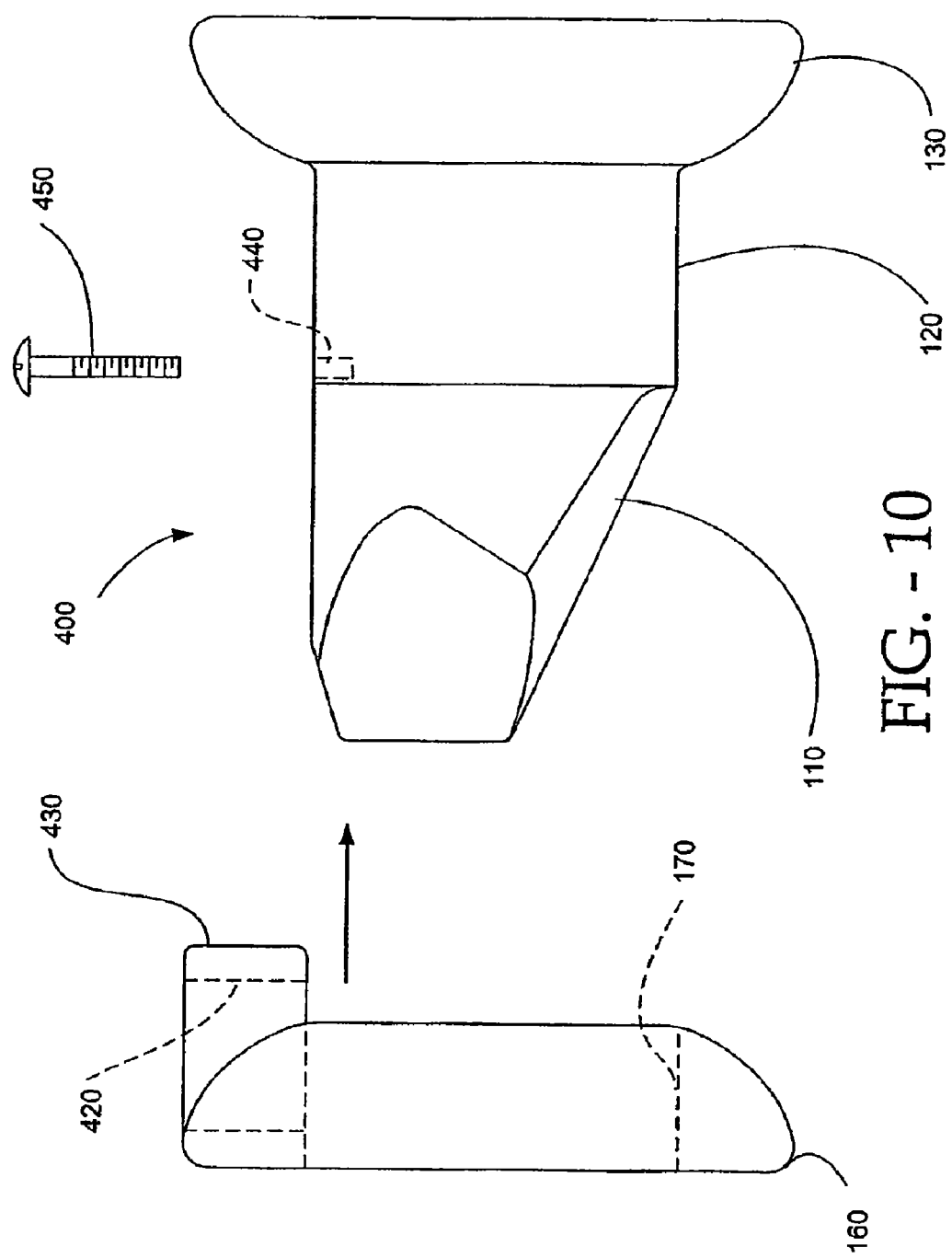
FIG. 10 is a plan view of an embodiment of an implant in accordance with the present invention wherein a screw is used to secure a second wing to the spacer.
Figure 11:
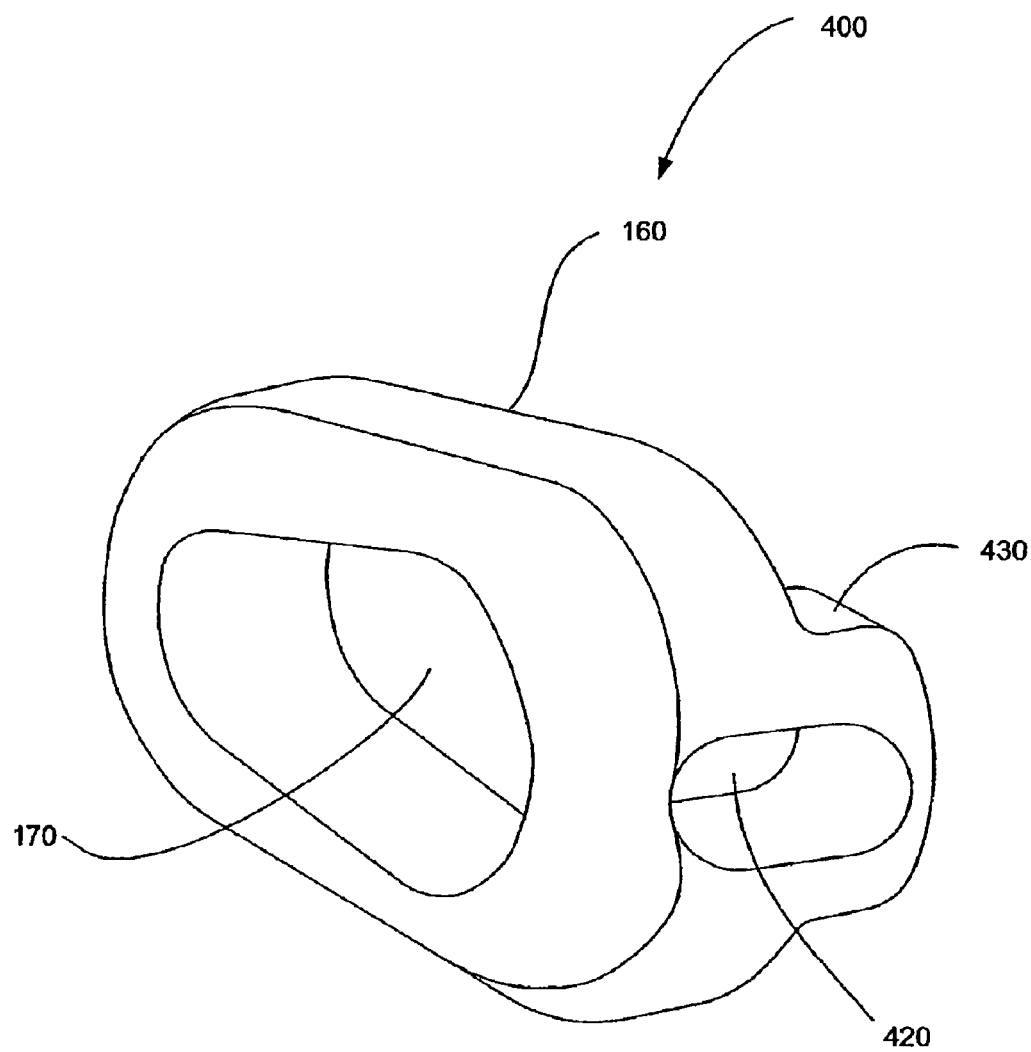
FIG. 11 is a perspective view of the second wing of FIG. 10.
Figure 12:
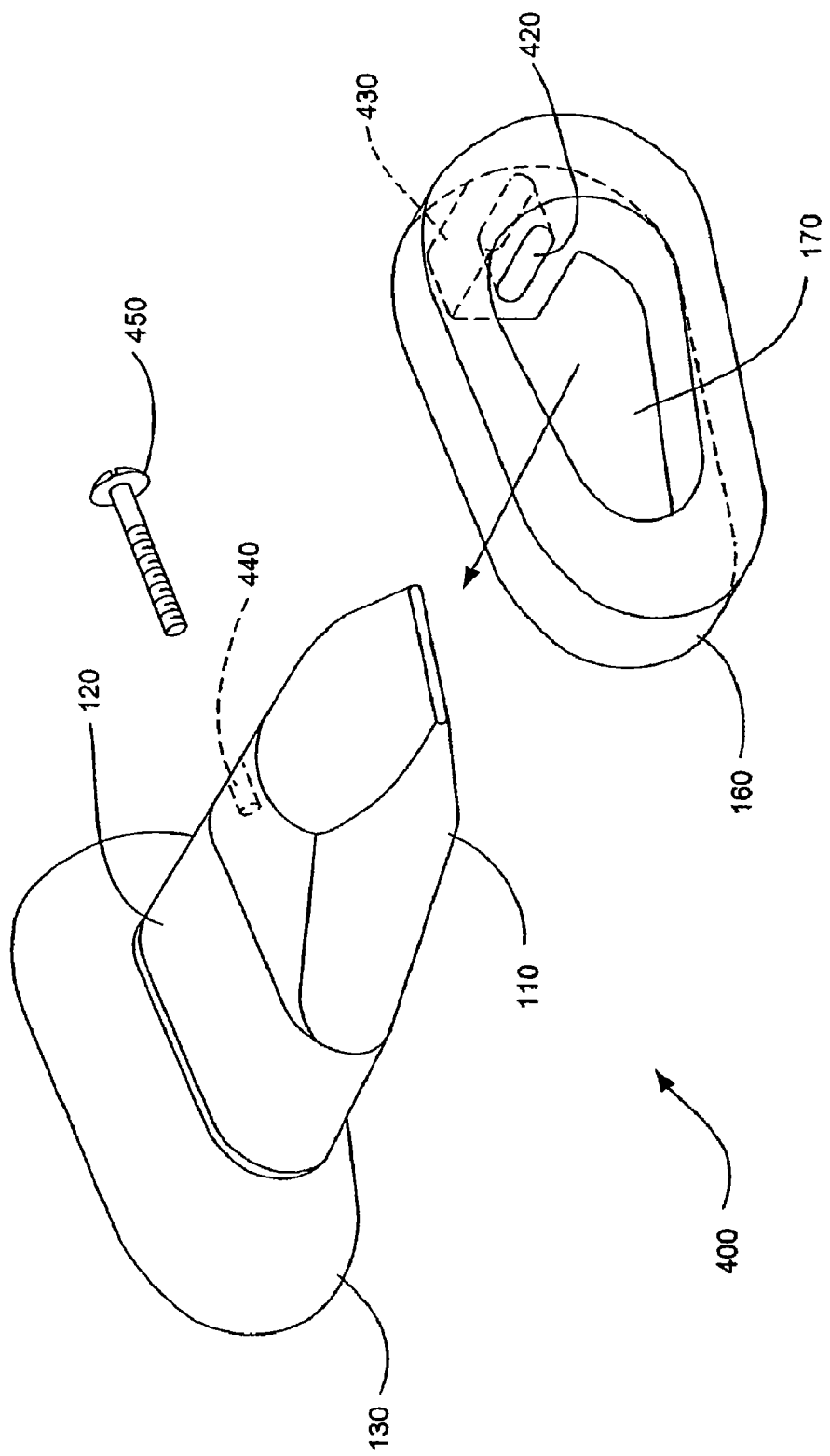
FIG. 12 is a perspective view of the implant of FIG. 10.
Figure 13A:
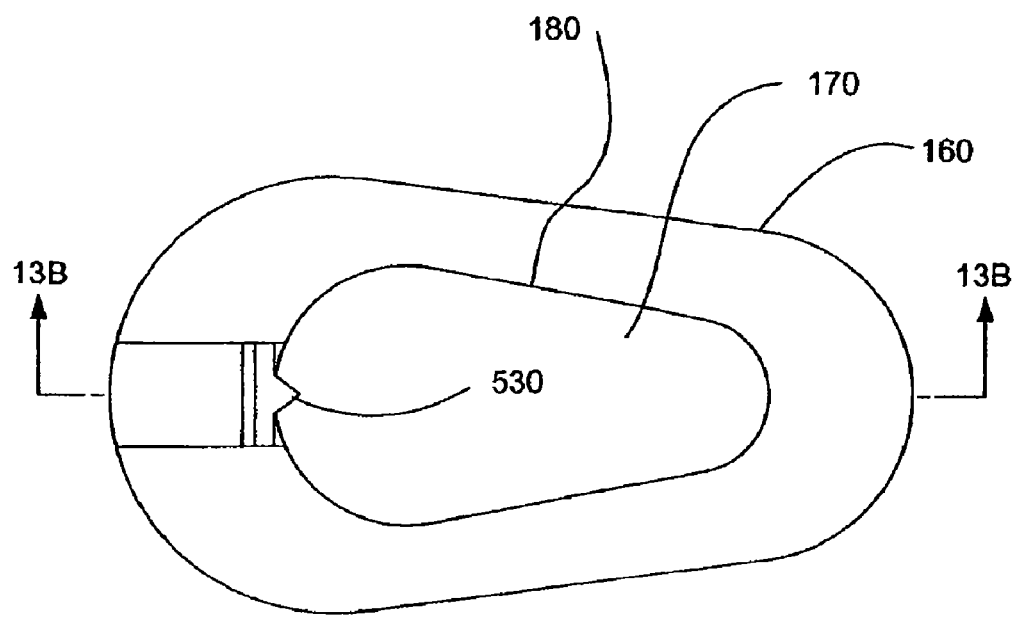
FIG. 13A is a front view of a second wing for use with some embodiments of implants of the present invention having a flexible hinge mechanism for securing the second wing to an implant.
Figure 13B:
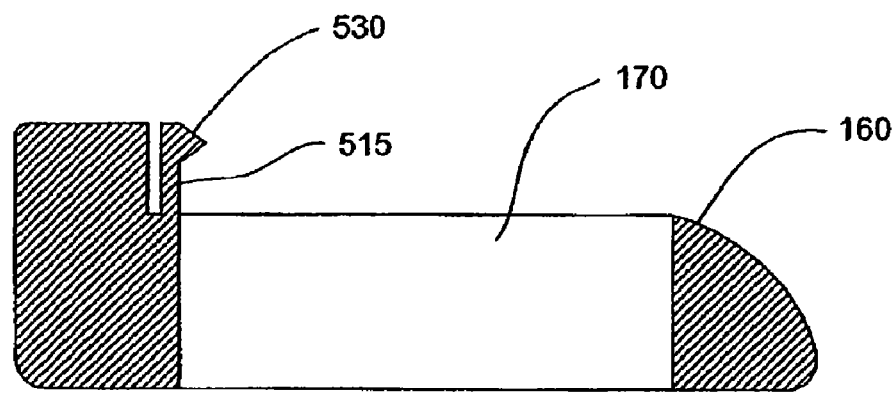
FIG. 13B is a side-sectional view of the second wing of FIG. 13A.
Figure 14A:
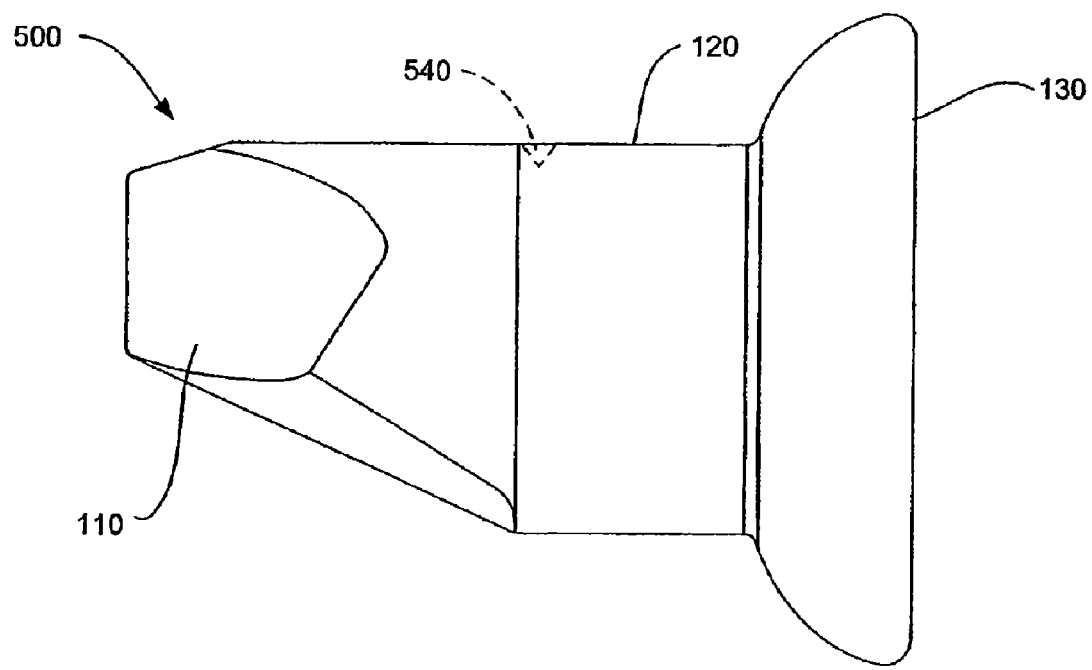
FIG. 14A is a plan view of an embodiment of an implant for use with the second wing of FIGS. 13A and 13B.
Figure 14B:
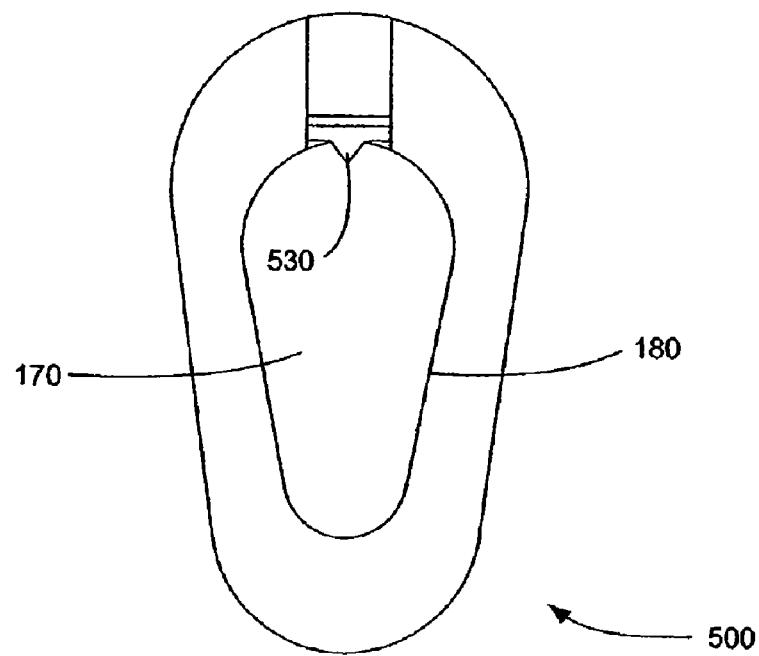
FIG. 14B is a front view of the second wing of FIGS. 13A and 13B.

With respect to the prior embodiments which have first and second wings 130,160, the second wing 160, can be designed to be interference-fit onto the spacer 120 (where the spacer is fixed) or a portion of the distraction guide 110 adjacent to the spacer 120 (where the spacer is rotatable). Where the second wing 160 is interference-fit, there is no additional attachment device to fasten the second wing 160 relative to the remainder of the implant. Alternatively, various fasteners can be used to secure the second wing relative to the remainder of the implant. For example, FIGS. 10-12 illustrate an embodiment of an implant 400 including a teardrop-shaped second wing 460 having a bore 463 through a tongue 461 at the posterior end of the second wing 460. The bore 463 is brought into alignment with a corresponding bore 440 on the spacer 120 when the second wing 460 is brought into position by surgical insertion relative to the rest of the implant 400. A threaded screw 442 can be inserted through the aligned bores 463,440 in a posterior-anterior direction to secure the second wing 460 to the spacer 120. The direction of insertion from a posterior to an anterior direction has the screw 442 engaging the bores 463,440 and the rest of the implant 400 along a direction that is generally perpendicular to the longitudinal axis 125. This orientation is most convenient when the surgeon is required to use a screw 442 to secure the second wing 460 to the rest of the implant 400. Other securing mechanisms using a member inserted into corresponding bores 463,440 on the spacer 120 and second wing 460 are within the spirit of the invention. It should be understood that a rotatable spacer 220 also can be accommodated by this embodiment. With a rotatable spacer 220, the second wing 460 would be attached to a portion of the distraction guide 110 that is located adjacent to the rotatable spacer 220.

FIGS. 13A-14B depict a further embodiment 500 wherein the second wing 560 is secured to the spacer 120 by a mechanism including a flexible hinge 565, with a protrusion 561 on the end of the hinge 565 adjacent to the lip 562 of the opening 564 defined by portions of the second wing 560. The securing mechanism also encompasses an indentation 540 on the spacer 120, wherein the indentation 540 accommodates the protrusion 561 on the end of the flexible hinge 565. During surgery, after insertion of the distraction guide 110, spacer 120, and first wing 130, the second wing 560 is received over the distraction guide 110 and the spacer 120. As the second wing 560 is received by the spacer 120, the flexible hinge 565 and its protrusion 561 deflect until the protrusion 561 meets and joins with the indentation 540 in the spacer 120, securing the second wing 560 to the spacer 120. Again in embodiments where the spacer can rotate, the indentation 540 is located on an end of the distraction guide 110 that is adjacent to the rotatable spacer 220. With respect to the flexible hinge 565, this hinge is in a preferred embodiment formed with the second wing 560 and designed in such a way that it can flex as the hinge 565 is urged over the distraction guide 110 and the spacer 120 and then allow the protrusion 561 to be deposited into the indentation 540. Alternatively, it can be appreciated that the indentation 540 can exist in the second wing 560 and the flexible hinge 565 and the protrusion 561 can exist on the spacer 120 in order to mate the second wing 560 to the spacer 120. Still alternatively, the flexible hinge 565 can be replaced with a flexible protrusion that can be flexed into engagement with the indentation 540 in the embodiment with the indentation 540 in the spacer 120 or in the embodiment with the indentation 540 in the second wing 560. One of ordinary skill in the art will appreciate the myriad different ways with which the second wing can be mated with the implant.

Figure 15A:
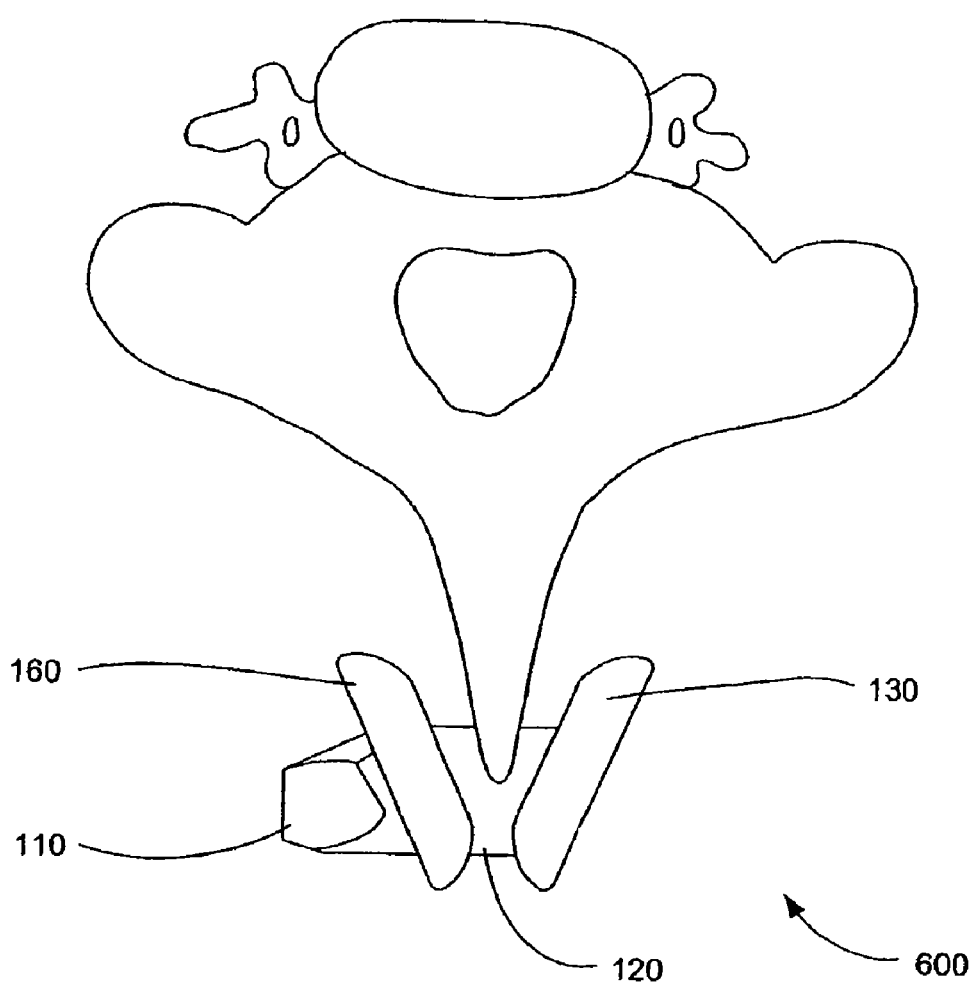
FIG. 15A is a top view of an embodiment of an implant in accordance with the present invention positioned between spinous processes of adjacent cervical vertebrae.
Figure 15B:
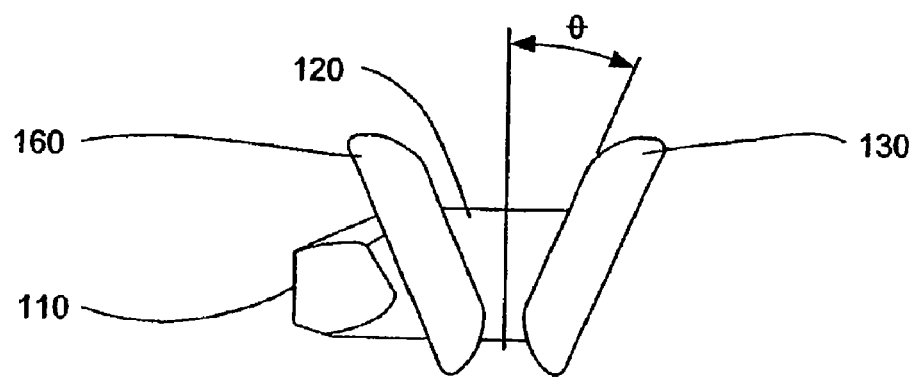
FIG. 15B is a top view of the implant of FIG. 15A showing wing orientation.
Figure 16:
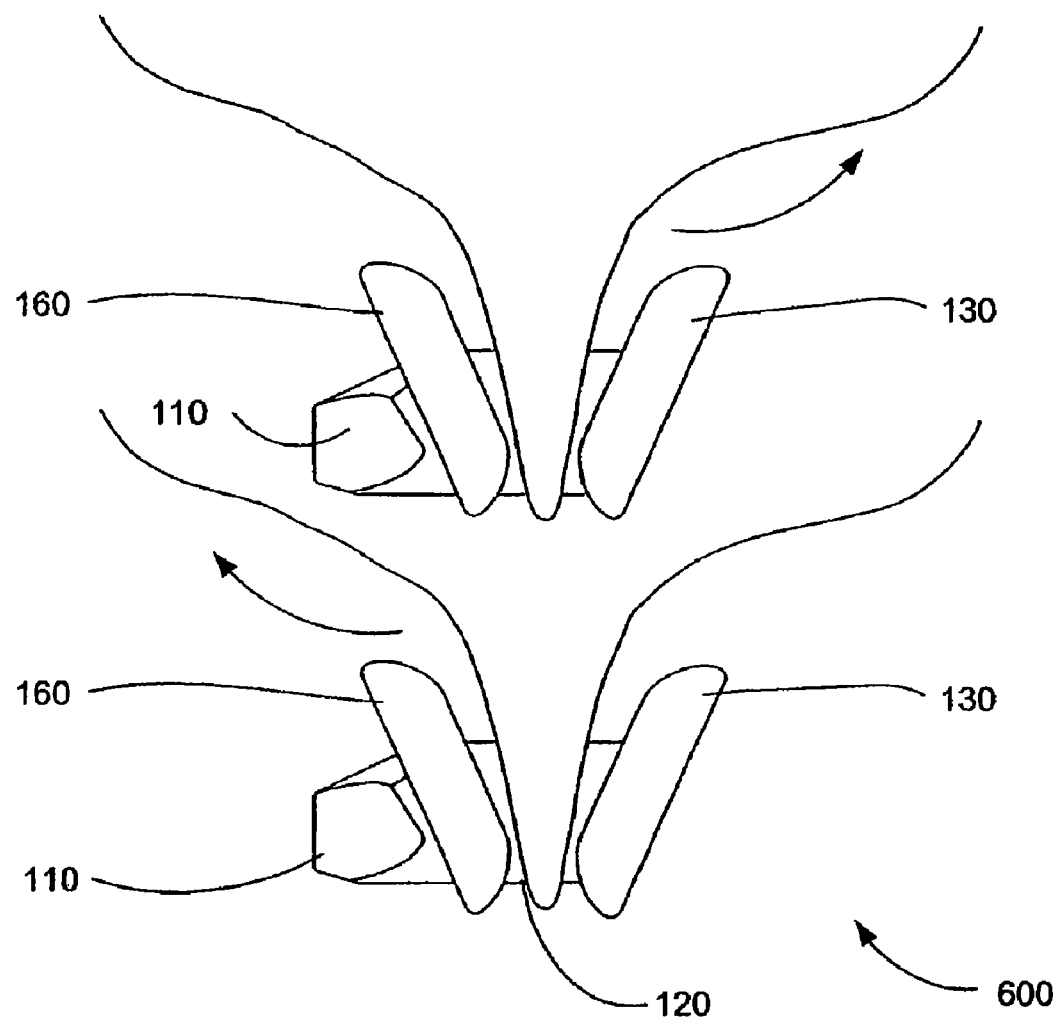
FIG. 16 is a top view of two such implants of the invention of FIGS. 15A and 15B, positioned in the cervical spine.

FIGS. 15A-16 illustrate an embodiment of an implant 600 wherein anterior ends of a first wing 630 and second wing 660 flare out at an angle away from the spacer 120 and away from each other. The cervical spinous processes are themselves wedge-shaped when seen from a top view. The first wing 630 and second wing 660 flare out so that the implant 600 can roughly conform with the wedge shape of the spinous processes, allowing the implant 600 to be positioned as close as possible to the vertebral bodies of the spine where the load of the spine is carried. The first and second wings 630,660 are positioned relative to the spacer, whether the spacer is fixed 120 or rotatable 220, so that the wings flare out as the wings approach the vertebral body of the spine. FIG. 15B is a top view of the implant 600 of FIG. 15A removed from proximity with the spinous processes. The first wing 630 is aligned at an angle with respect to an axis along the spinous processes perpendicular to the longitudinal axis (also referred to herein as the plane of symmetry). In one embodiment, the angle is about 30°, however, the angle .theta. can range from about 15° to about 45°. In other embodiments, other angles outside of this range are contemplated and in accordance with the invention. Likewise, the second wing 660 can be aligned along a similar, but oppositely varying range of angles relative to the plane of symmetry.

As described above in reference to FIG. 4, the second wing 660 defines an opening which is outlined by a lip. As is evident, the lip can be provided at an angle relative to the rest of the second wing 660 so that when the lip is urged into contact with the spacer 120, the second wing 660 has the desired angle relative to the spacer 120. As discussed above, there are various ways that the second wing 660 is secured to the spacer 120. FIG. 15A depicts a top view of one such implant 600 placed between the spinous processes of adjacent cervical vertebrae. FIG. 16 is a top view illustrating two layers of distracting implants 600 with flared wings 630,660.

Figure 17:
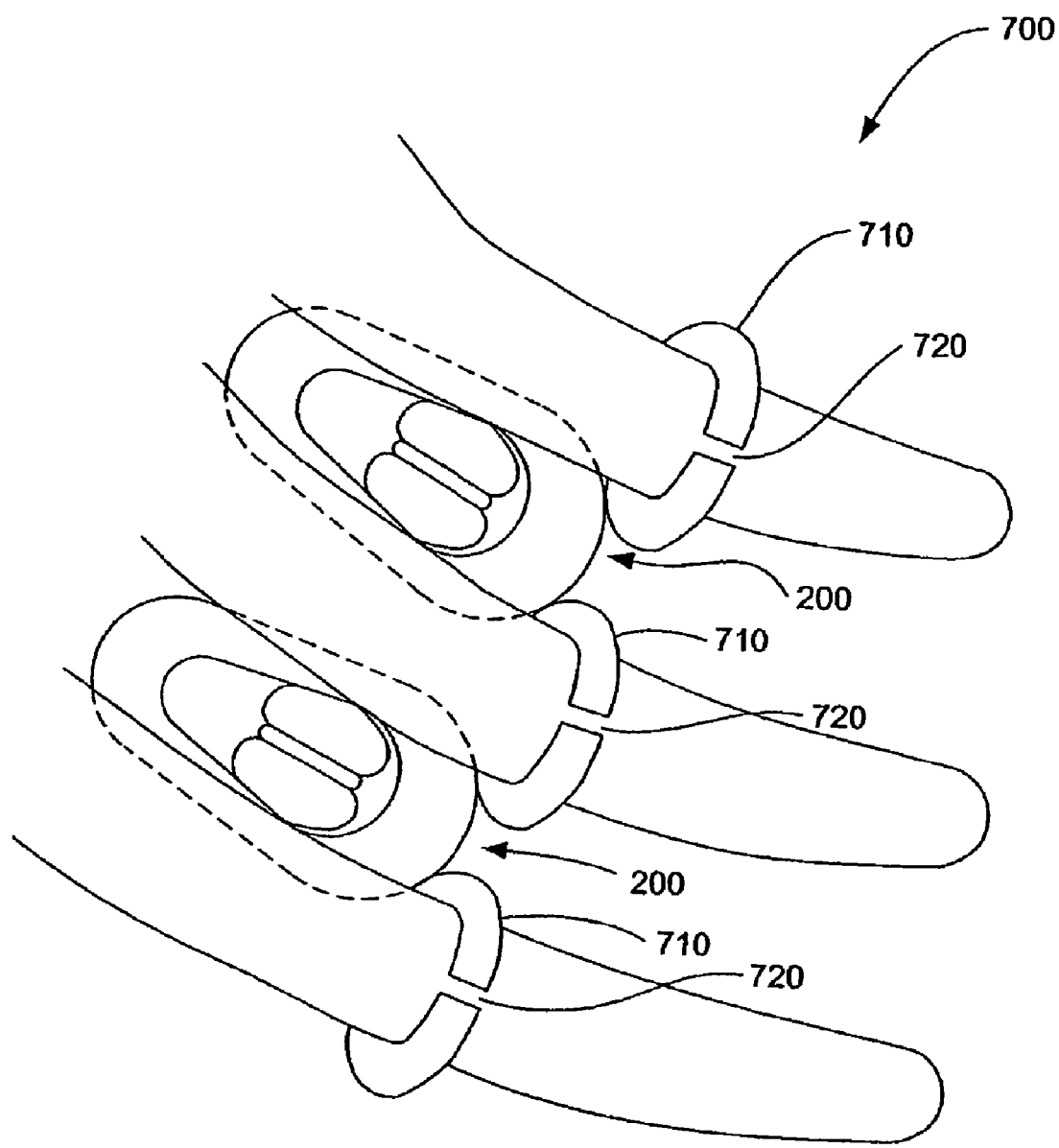
FIG. 17 is a side view of two implants of the invention positioned in the cervical spine, with stops or keeps at the proximal ends of the spinous processes.

Systems and methods in accordance with the present invention can include devices that can be used in cooperation with implants of the present invention. FIG. 17 illustrates "stops" (also referred to herein as "keeps") 656, which are rings of flexible biocompatible material, which can be positioned around the spinous processes of adjacent cervical vertebrae and located posteriorly to the implant 600. The keeps 656 can prevent posterior displacement of implants. In one embodiment, the keeps can include a ring having a slit 658. The keeps 656 can be somewhat sprung apart, so that the keep 656 can be fit over the end of the spinous process and then allowed to spring back together in order to hold a position on the spinous process. The keep 656 can act as a block to the spacer 120 in order to prevent the implant 600 from movement in a posterior direction.

Implants Having Deployable Wings

Figure 18A:
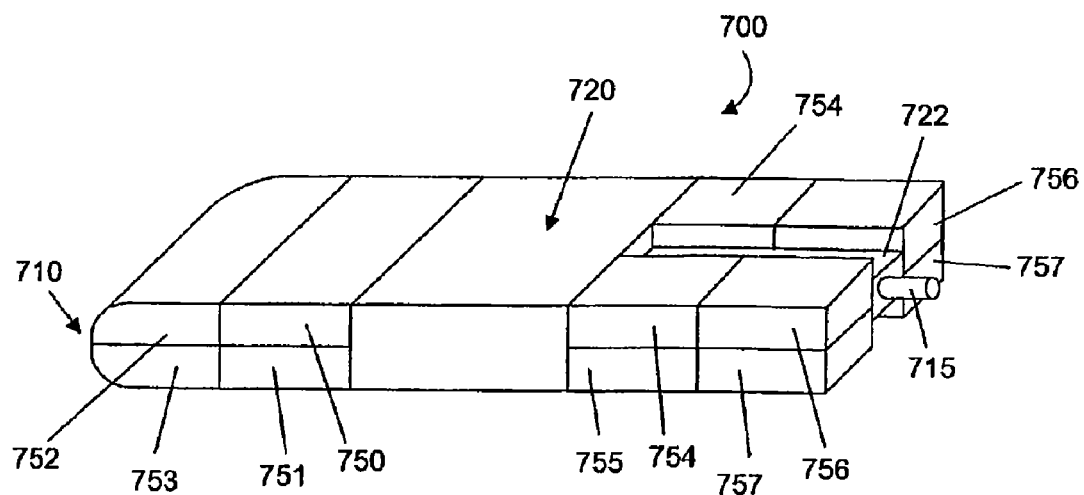
FIG. 18A is a perspective view of an alternative embodiment of an implant in accordance with the present invention having a first wing and a second wing that can be deployed after arranging the implant between adjacent spinous processes.
Figure 18B:
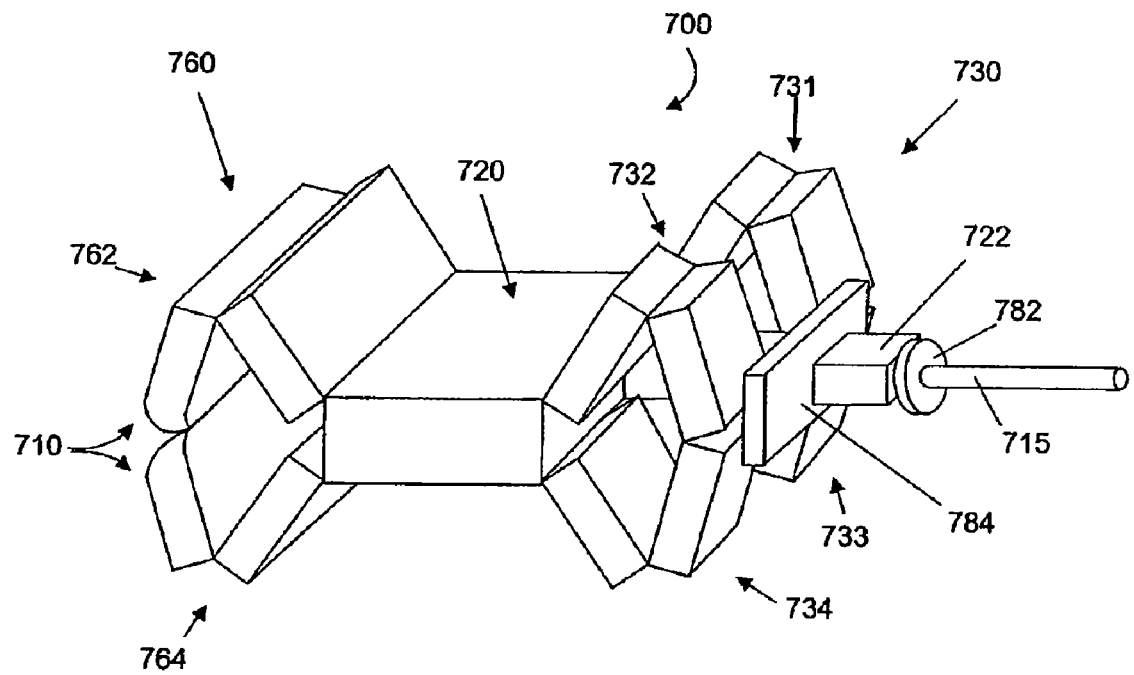
FIG. 18B is a perspective view of the implant of FIG. 18B in a deployed configuration.

In other embodiments, implants in accordance with the present invention can comprise a "matchbox"-like structure having a first configuration (as shown in FIG. 18A) and a second, deployed configuration (as shown in FIG. 18B). Arranged in the first configuration, such implants 700 can have a substantially flat profile having an approximately uniform thickness. The uniform thickness approximates the thickness of a spacer 720 of the implant 700. The implant 700 can comprise a distraction guide 710 at a proximal end of the implant, the distraction guide 710 having a slightly rounded or tapered shape to pierce and/or distract a space between adjacent spinous processes. The implant 700 can further comprise a plurality of hinged structures 750-757, the hinged structures 750-757 being collapsed so as to facilitate the substantially flat profile. The hinged structures 750-757 are pivotally connected with the spacer 720 and extend from both sides of the spacer 720. As shown in FIG. 18A, a support structure 722 extends from the spacer 720 toward the distal end of the implant 700. A rod 715 (or alternatively some other mechanism such as a tab) can be connected with the proximal end of the implant 700 and can extend through the hinged structures 750-753, through the spacer 720, and through the support structure 722 so that the rod 715 is accessible.

Referring to FIG. 18B, once the implant 700 is positioned as desired between adjacent spinous processes, the rod 715 can be drawn in a direction opposite the direction of insertion along the longitudinal axis 725 so that the hinged structures 750-757 fold outward to form a first wing 730 and a second wing 760 between which is arranged the spacer 720 and a portion of the spinous processes. As the hinged structures 750-757 fold outward, the height of the first and second wings 730,760 increases from approximately the same as the thickness of the spacer 720 to a height such that the first and second wing 730,760 can limit or block movement of the implant 700 along the longitudinal axis 725 when positioned between adjacent spinous processes. As can be seen, the second wing 760 includes four hinged structures 750-753: an upper first structure 750 connected by a hinge to an upper second structure 752, and a lower first structure 751 connected by a hinge to a lower second structure 753. The hinged structures 750-753 pivot outward to form an upper end 762 of the second wing and a lower end 764 of the second wing. Likewise, the first wing 730 includes four hinged structures 754-757: an upper first structure 754 connected by a hinge to an upper second structure 756, and a lower first structure 755 connected by a hinge to a lower second structure 757. However, unlike the second wing 760, the first wing 730 is (effectively) bisected by the support structure 722 so that the first wing 730 comprises four winglets 731-734. The hinged structures 754-757 pivot outward to form upper winglets 731,732 of the first wing and lower winglets 733,734 of the first wing.

As mentioned above, the support structure 722 extends from the spacer 720 toward the distal end of the implant 700. The spacer 720 and the support structure 722 include a bore or other cavity through which the rod 715 can travel. Applying resistive force to the support structure 722 can fix the spacer 720 in place between spinous processes when drawing the rod 715 through the bore. As the rod 715 is drawn through the bore, the hinged structures 752,753 with which the proximal end of the rod 715 is connected are drawn with the rod 715. As the rod 715 is drawn through the spacer 720, the hinged structures 752,753 are drawn toward the spacer 720. The hinged structures 750-753 pivot outward to accommodate the relative movement between the rod 715 and the spacer 720. Accordingly, the second wing 760 has been satisfactorily deployed.

The hinged structures 756,757 of the first wing 730 can cause deployment of the first wing 730 by applying resistive force to the hinged structures 756,757 while drawing the spacer 720 (via the support structure 722), or by urging the hinged structures 756,757 toward the spacer 720. The resistive force or urging can be applied by a second stop 784 that can fit around the support structure 722 and can be interference fit or otherwise selectively fixed with the support structure 722. As the second stop 784 is pushed along the longitudinal axis 725, along the support structure 722, the hinged structures 754-757 pivot outward to accommodate the relative movement between the second stop 784 and the spacer 720. Accordingly, the first wing 730 has been satisfactorily deployed.

Figure 19A:
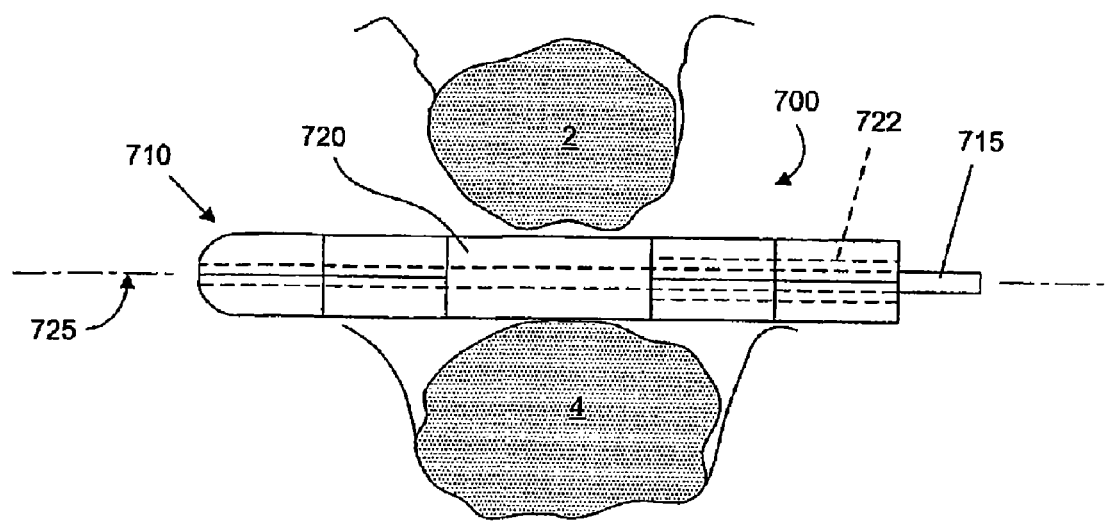
FIG. 19A is a posterior view of the implant of FIGS. 18A and 18B positioned between adjacent spinous processes in an undeployed configuration.
Figure 19B:
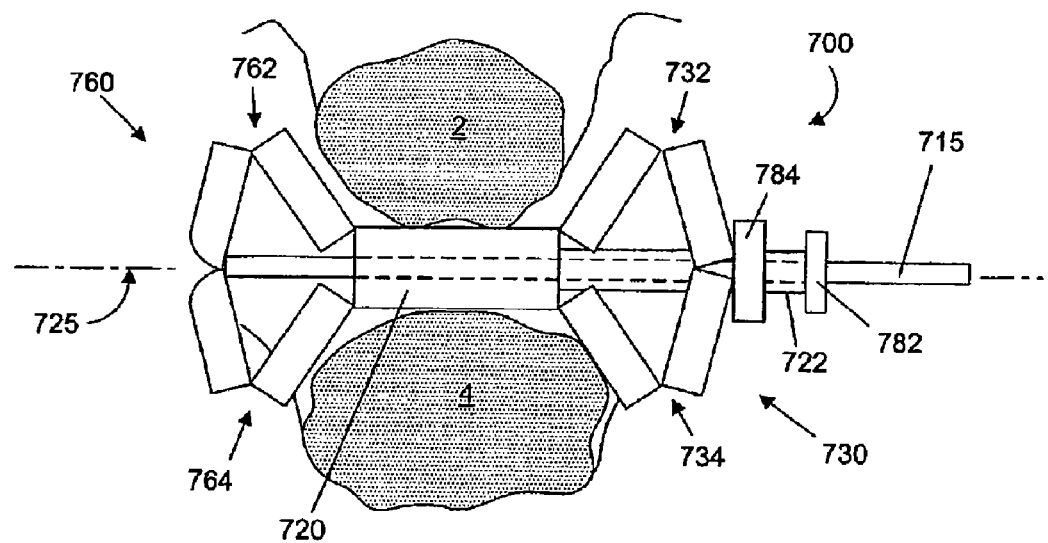
FIG. 19B is a posterior view of the implant of FIGS. 18A and 18B positioned between adjacent spinous processes in a deployed configuration.

FIGS. 19A and 19B are posterior views of the implant 700 positioned between adjacent spinous processes 2,4 demonstrating an embodiment of a method for deploying the implant 700 between the spinous processes 2,4. The implant 700 can be positioned so that a distraction guide 710 of the implant 700 is arranged at a space between the spinous processes 2,4. The implant 700 can then be urged between the spinous processes 2,4 so that the spacer 720 is positioned as desired. The substantially flat profile of the implant 700 can ease positioning of the spacer 720 by reducing potential obstructing surfaces that can resist movement of the implant 700 during implantation. The second wing 760 and the first wing 730 can then be deployed to limit movement of the implant 700. To deploy the second wing 760 the rod 715 is drawn in a direction opposite the direction of insertion along the longitudinal axis 725. The upper end 762 and lower end 764 of the second wing extend outward as described above. Once the second wing 760 is deployed, the rod 715 can be fixed in position relative to the spacer 720. This can be accomplished using myriad different mechanisms. For example, as shown a first stop 782 can be interference fit to the rod 715 and positioned against the support structure 722 along the rod 715. The first stop 782 can grip the rod 715, as with a friction fit between the first stop 782 and the rod 715, so that the rod 715 is prevented from moving through the bore of the support structure 722 by interference between the first stop 782 and the support structure 722. In other embodiments, some other mechanism can be used, such as a pin (e.g., a cotter pin), a latch system, etc. One of ordinary skill in the art will appreciate the myriad different mechanisms for fixing a rod 715 in position relative to the spacer 720. The upper second structure 756 and the lower second structure 757 can be urged toward the spacer 720 in the direction of insertion along the longitudinal axis 725 using a second stop 784 as described above, causing the upper winglets 731,732 and lower winglets 733, 734 to extend outward to form the first wing 730. Once the first wing 730 is deployed, the hinged structures 754-757 can be fixed in position using the second stop 784 or some other mechanism. The second stop 784 can grip the support structure 722, as with a friction fit or pin, and resist movement of the hinged structures 754-757, thereby preventing collapse. As above, one of ordinary skill in the art will appreciate the myriad different mechanisms for fixing the first wing 730 in a deployed position. With the first wing 730 and the second wing 760 deployed, movement of the implant 700 along the longitudinal axis 725 can be limited or blocked, thereby resisting undesirable displacement of the implant 700.

It should be noted that with implants as described above in reference to FIGS. 18A-21 the rod 715 can optionally be trimmed or otherwise partially detached to decrease a space required to accommodate the implant 700,800 within the patient's spine. For example, the structure of the rod 715 can be beveled or otherwise weakened near a distal end of the rod 715 to allow the rod 715 to be snapped off when the first and second wings 730,760,830,860 are deployed and the rod 715 is fixed in place. In other embodiments, a tool (not shown) can be used to cut the rod 715 after the first and second wings 730,760,830,860 are deployed and the rod 715 is fixed in place. Still further, the rod 715 need not comprise a rigid structure, but rather alternatively can include a tether, string, or similarly flexible structure that can be placed in tension to retain the second wing 760,860 and/or first wing 730,830 in a deployed position.

Figure 20A:
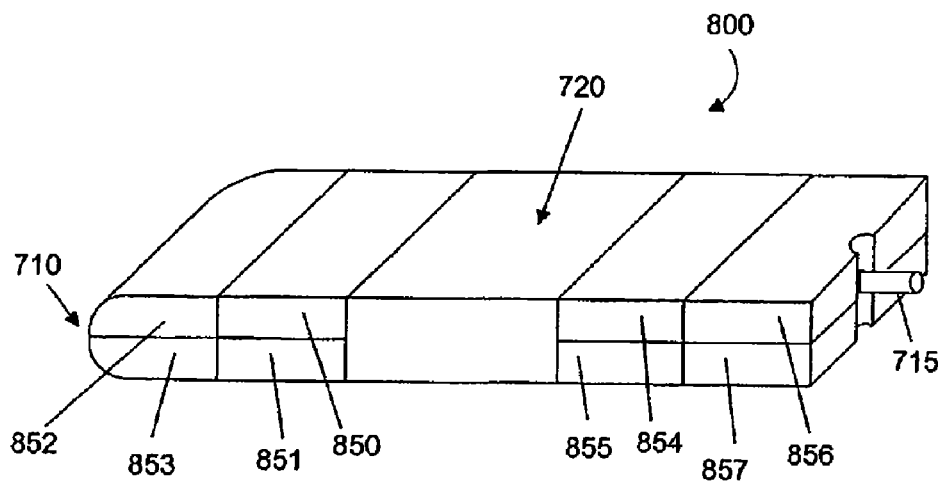
FIG. 20A is a perspective view of still another embodiment of an implant in accordance with the present invention having a first wing and a second wing that can be deployed after arranging the implant between adjacent spinous processes.
Figure 20B:
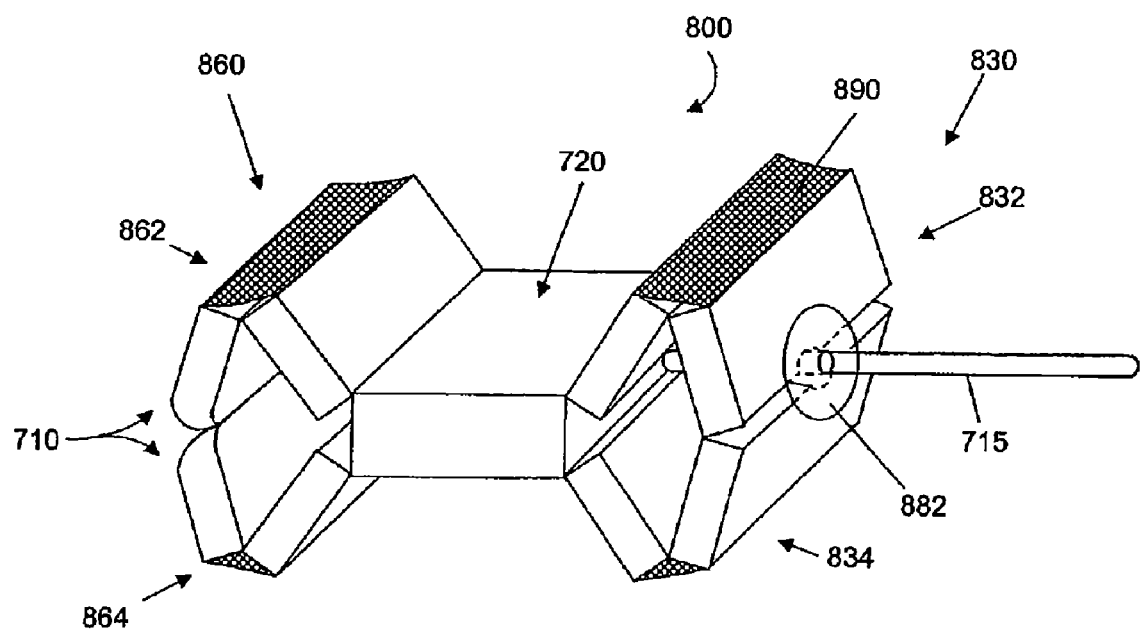
FIG. 20B is a perspective view of the implant of FIG. 20A in a deployed configuration.

Referring to FIGS. 20A and 20B, a still further embodiment of an implant 800 in accordance with the present invention is shown. In such an embodiment, a flexible strap 890 can be connected between pairs of hinged structures (i.e., 850 and 852, 851 and 853, 854 and 856, 855 and 857). The flexible strap 890 can limit the relative movement of the hinged structures 850-857 so that first wing 830 and second wing 860 have increased rigidity when fully deployed. The implant 800 need not include the support structure 722 of the previous embodiment. A resistive force can be applied to the hinged structures 856,857 so that as the rod 715 is drawn in a direction opposite the direction of insertion along the longitudinal axis 825 the resistive force causes the hinged structures 854-857 to extend outward to form the first wing 830. As the hinged structures 854-857 extend outward the flexible strap 890 connected opposite the hinge unfolds. Once the hinged structures 854-857 reach a maximum extension, the flexible strap 890 becomes taut and resists further extension, locking the first wing 830 in place. The flexible straps 890 can provide the first wing 830 with sufficient rigidity to resist movement of the spacer 720, so that as the rod 715 is further drawn the rod 715 moves through the spacer 720 and the hinged structures 852, 853 connected with the rod 715 are drawn toward the spacer 720. As the hinged structures 852,853 connected with the rod 715 are drawn toward the spacer 720, all of the hinged structures 850-853 extend outward to deploy the second wing 860. The flexible strap 890, connected opposite the hinge, unfolds. Once the hinged structures 854-857 reach a maximum extension the flexible strap 890 becomes taut and resists further extension, locking the first wing 830 in place. A stop 882 (or alternatively some other mechanism such as a pin) can be fixed to the rod 715 to create interference between the stop 882 and the hinged structures 832,834 of the first wing 830 that resists movement of the rod 715.

The flexible straps 890 can be made from a biocompatible material. In an embodiment, the flexible straps 890 can be made from a braided polyester suture material. Braided polyester suture materials include, for example, Ethibond, Ethiflex, Mersilene, and Dacron, and are non-absorbable, having high tensile strength, low tissue reactivity and improved handling. In other embodiments, the flexible straps 890 can be made from stainless steel (i.e., surgical steel), which can be woven into a strap, for example. In still other embodiments, flexible straps 890 can be made from some other material (or combination of materials) having similar properties.

Figure 21:
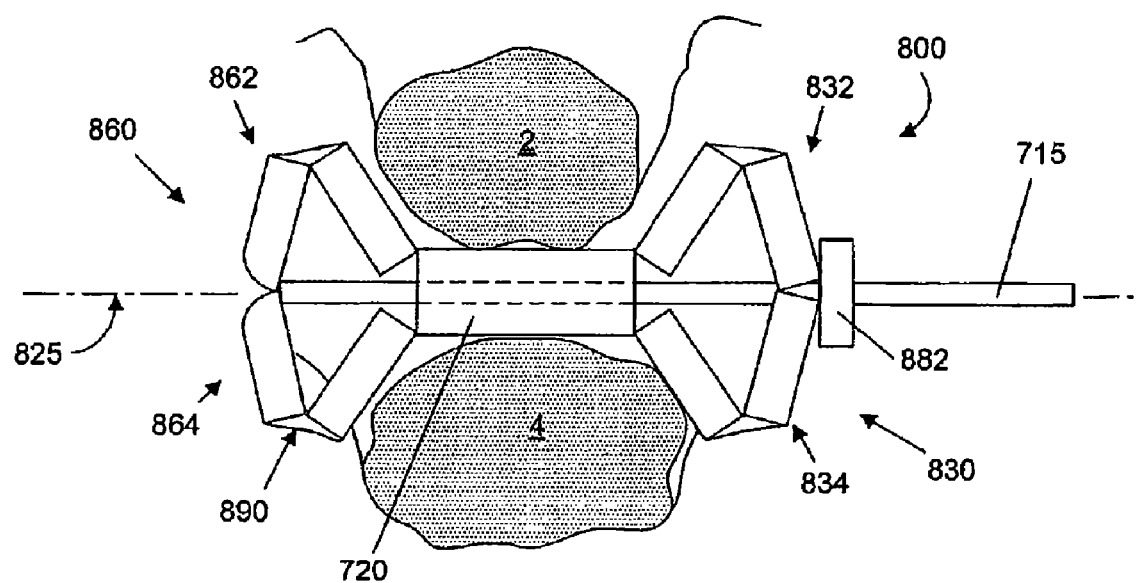
FIG. 21 is a posterior view of the implant of FIGS. 20A and 20B positioned between adjacent spinous processes in a deployed configuration.

FIG. 21 is a posterior view of the implant 800 positioned between adjacent spinous processes 2,4 demonstrating an embodiment of a method for deploying the implant 800 between the spinous processes 2,4. The first wing 830 can be deployed to limit movement of the implant 800 relative to the spinous processes 2,4. To deploy the first wing 830 the rod 715 can be held fixed in position or urged in a direction opposite the direction of insertion along the longitudinal axis 825 while a force is applied to the hinged structures 854-857 (FIG. 20A) of the first wing 830 to cause the upper end 832 of the first wing and the lower end 834 of the first wing to extend away from the rod 715, thereby deploying the first wing 830.

The rod 715 can be further urged in the direction opposite the direction of insertion so that the proximal end of the rod 715 pivotably connected with the hinged structures 852,853 that comprise the distraction guide 710, is drawn toward the spacer 720, causing the upper end 862 of the spacer, and the lower end 864 of the spacer to extend away from the rod 715. Once the second wing 860 and the first wing 830 are deployed, the rod 715 can be fixed in position relative to the spacer 720. As above, this can be accomplished using myriad different mechanisms. For example, as shown a first stop 882 can be interference fit to the rod 715 and positioned against the first wing 830 along the rod 715. The first stop 882 can grip the rod 715 so that the rod 715 is prevented from moving by a friction fit between the first stop 882 and the rod 715. In other embodiments, some other mechanism can be used, such as a pin (e.g., a cotter pin), a latch system, etc. One of ordinary skill in the art will appreciate the myriad different mechanisms for fixing a rod 715 in position relative to the spacer 720. With the first wing 830 and the second wing 860 deployed, movement of the implant 800 along the longitudinal axis 825 can be limited or blocked, thereby resisting undesirable displacement of the implant 800.

Figure 22A:
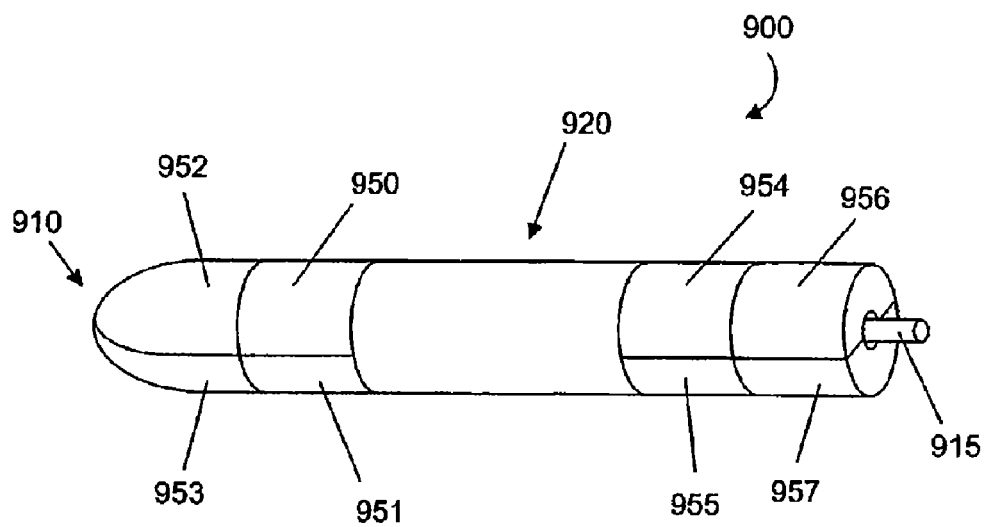
FIG. 22A is a perspective view of an alternative embodiment of an implant in accordance with the present invention having a first wing and a second wing that can be deployed after arranging the implant between adjacent spinous processes.
Figure 22B:
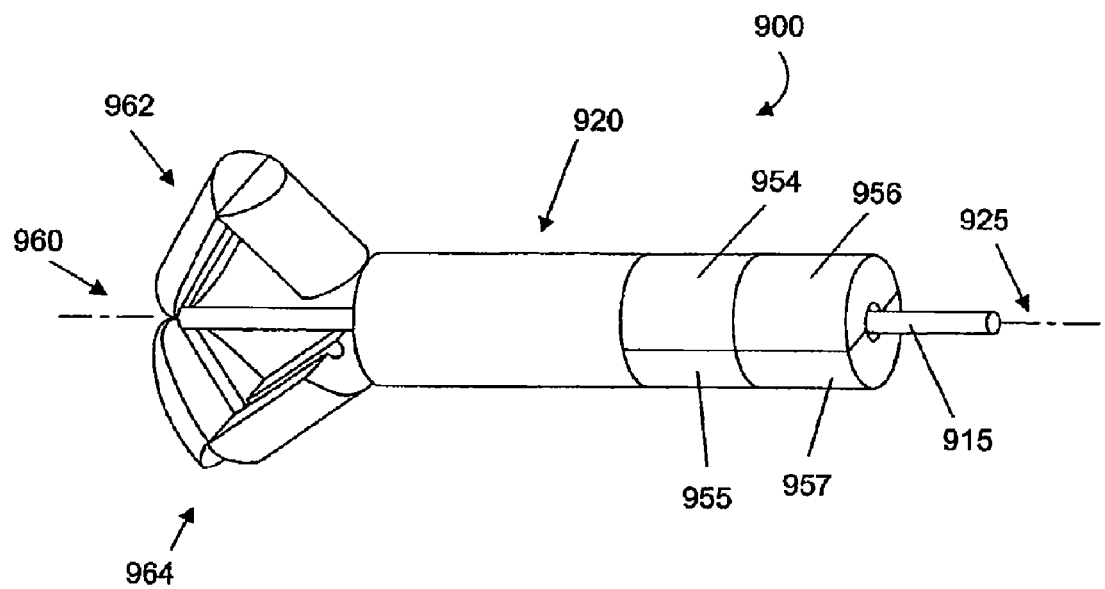
FIG. 22B is a perspective view of the implant of FIG. 22A in a partially deployed configuration.

Referring to FIGS. 22A and 22B, in still other embodiments, implants in accordance with the present invention can comprise a "matchbox"-like structure having a rounded, collapsed first configuration and a second, deployed configuration. Arranged in the first configuration, such implants 900 can have a shape allowing the implant 900 to be more naturally inserted through a cannula. As shown, such a shape includes a substantially circular cross-section, though in other embodiments the implant can have an ovoid or elliptical cross-section, thereby allowing a spacer shape to be employed that generally accommodates a space between adjacent spinous processes. However, it will be appreciated that an implant 900 having a circular cross-section can most efficiently use the space of a cannula, where the cannula includes a circular cross-section; therefore, it may be preferable to employ an implant 900 having a circular cross-section where a physician desired to minify the diameter of the cannula inserted into the surgical site.

The cross-section of the implant 900 in a first configuration is generally consistent along the implant's length, having a diameter generally the thickness of a spacer 920 of the implant 900. The implant 900 can comprise a distraction guide 910 at a proximal end of the implant 900, the distraction guide 910 having a rounded (as shown) or tapered shape to pierce and/or distract a space between adjacent spinous processes. However, where a cannula is employed to deliver an implant to a surgical site, the implant 900 can optionally include a distraction guide 910 at the proximal end. The surgical site, and associated tissues and structures can be distracted and repositioned by the cannula, allowing substantially unobstructed access to the surgical site by the implant 900. In such circumstance a distraction guide 910 may not be necessary.

The implant 900 can further comprise a plurality of hinged structures 950-957, the hinged structures 950-957 being collapsed so as to facilitate the substantially collapsed profile. The hinged structures 950-(57 are pivotally connected with the spacer 920 and extend from both sides of the spacer 920. A rod 915 (or alternatively some other mechanism such as a tab) can be connected with the proximal end of the implant 900 and can extend through the hinged structures 950-953, and through the spacer 920 so that the rod 915 is accessible to a physician.

Figure 22C:
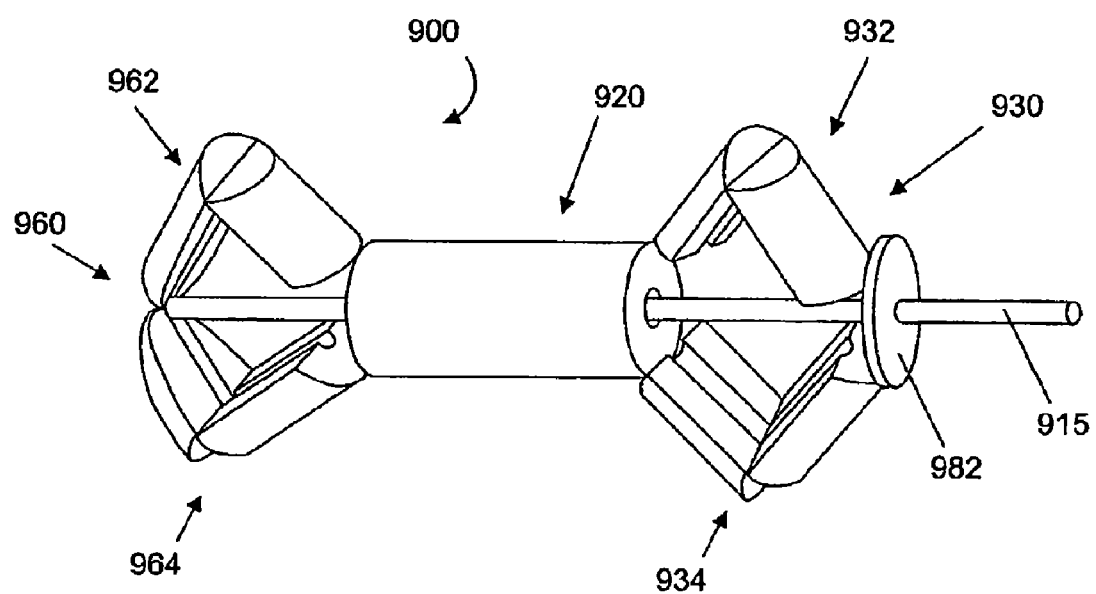
FIG. 22C is a perspective view of the implant of FIG. 22A in a fully deployed configuration.

Referring to FIGS. 22B and 22C, once the implant 900 is positioned as desired between adjacent spinous processes, the rod 915 can be drawn in a direction opposite the direction of insertion along the longitudinal axis 925 so that the hinged structures 950-957 fold outward to form a first wing 930 and a second wing 960 between which is arranged the spacer 920 and a portion of the spinous processes. As the hinged structures 950-957 fold outward, the height of the first and second wings 930,960 increases from approximately the same as the thickness of the spacer 920 to a height such that the first and second wing 930,960 can limit or block movement of the implant 900 along the longitudinal axis 925 when positioned between adjacent spinous processes. As can be seen, the second wing 960 includes four hinged structures 950-953: an upper first structure 950 connected by a hinge to an upper second structure 952, and a lower first structure 951 connected by a hinge to a lower second structure 953. The hinged structures 950-953 pivot outward to form an upper end 962 of the second wing and a lower end 964 of the second wing. Likewise, the first wing 930 includes four hinged structures 954-957: an upper first structure 954 connected by a hinge to an upper second structure 956, and a lower first structure 955 connected by a hinge to a lower second structure 957.

Figure 23A:
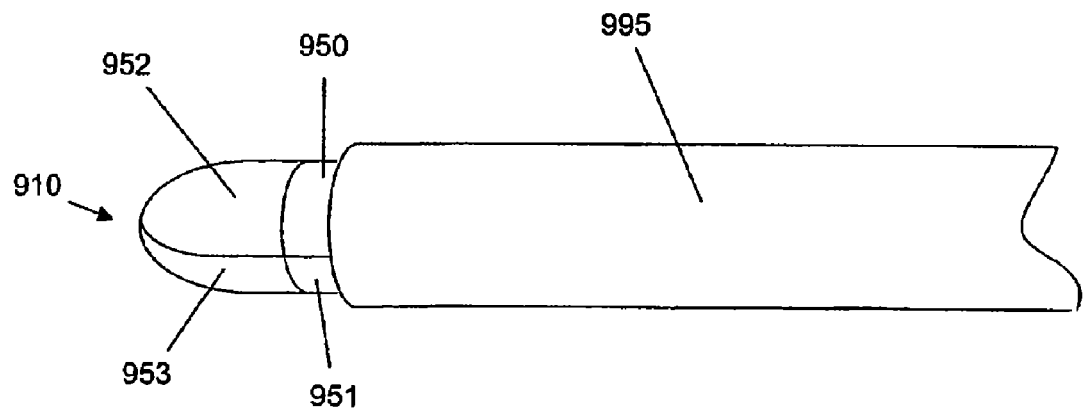
FIG. 23A is a perspective view of the implant of FIG. 22A including a cannula within which the implant is disposed for insertion into desired location between adjacent spinous processes.
Figure 23B:
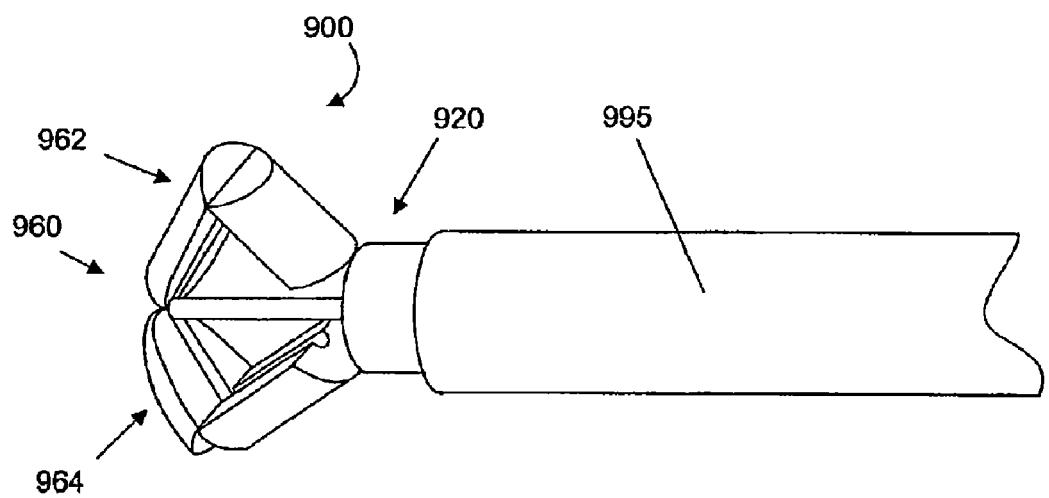
FIG. 23B is a perspective view of the implant of FIG. 23A in a partially deployed configuration.
Figure 23C:
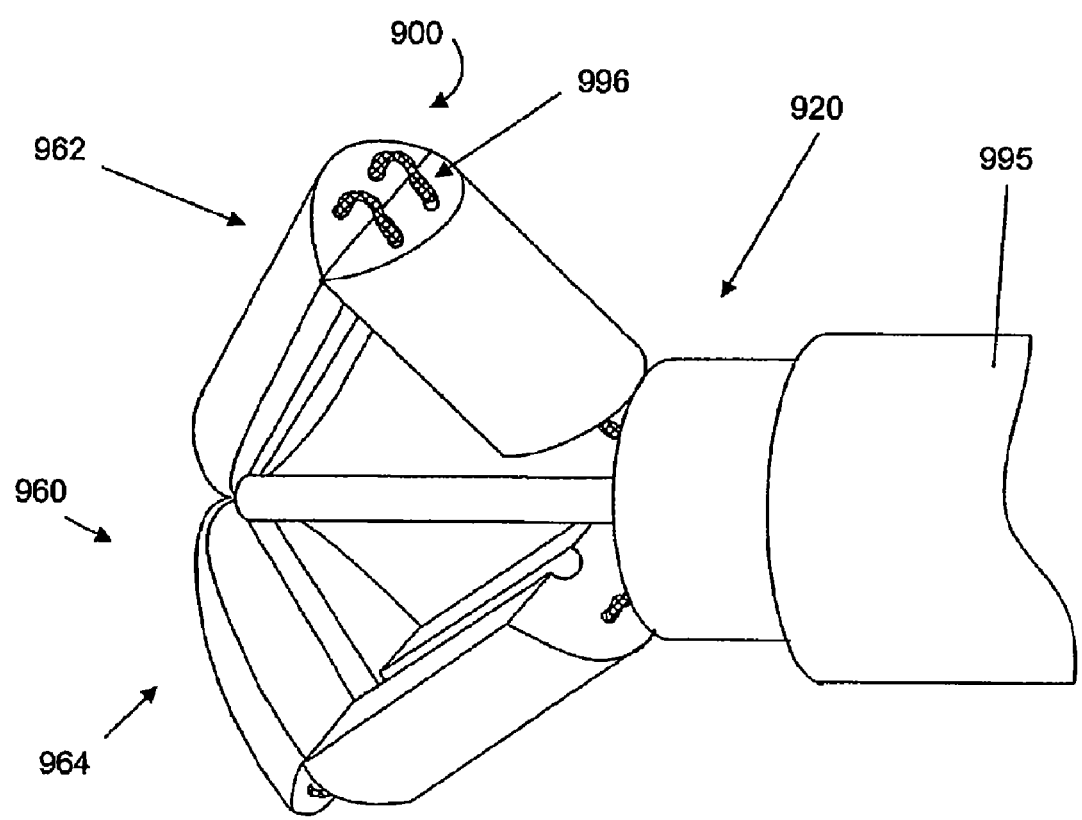
FIG. 23C is a perspective close-up view of the implant of FIG. 23A showing hinged structures connected by cords.

Embodiments as described above in reference to FIGS. 18A and 18B included a support structure 722 extending from the spacer 720. Likewise, a support structure can optionally extend from the spacer 920 of the cannula delivered implant 900. However, such a structure need not be necessary where the first wing 930 is prevented from deploying during deployment of the second wing 960 by the cannula 995 itself (see FIG. 23B). Referring to FIGS. 23A and 23B, once the cannula is positioned at the surgical site, the implant 900 can be urged through the cannula so that the hinged structures 950-953 are clear of the cannula. The rod 915 can then be urged in an opposite direction (relative to insertion) along the longitudinal axis 925 to deploy the second wing 960. As the rod 915 is drawn through the spacer 920, the hinged structures 952,953 are drawn toward the spacer 920. The hinged structures 950-953 pivot outward to accommodate the relative movement between the rod 915 and the spacer 920. Accordingly, the second wing 960 has been satisfactorily deployed.

Once the second wing 960 is deployed, the cannula 995 can be retracted from the surgical site, thereby allowing the hinged structures 956,957 of the first wing 930 to deploy by urging the hinged structures 956,957 toward the spacer 920. The urging can be applied by a stop 982 that can fit around the rod 915 and can be interference fit or otherwise selectively fixed with the rod 915. As the stop 982 is pushed along the longitudinal axis 925, along the rod 915, the hinged structures 954-957 pivot outward to accommodate the relative movement between the stop 982 and the spacer 920. Accordingly, the first wing 930 has been satisfactorily deployed.

Once the second wing 960 and the first wing 930 are deployed, the rod 915 can be fixed in position relative to the spacer 920. As above, this can be accomplished using myriad different mechanisms. For example, as shown a stop 982 can be interference fit to the rod 915 and positioned against the first wing 930 along the rod 915. The stop 982 can grip the rod 915 so that the rod 915 is prevented from moving by a friction fit between the stop 982 and the rod 915. In other embodiments, some other mechanism can be used, such as a pin (e.g., a cotter pin), a latch system, etc. One of ordinary skill in the art will appreciate the myriad different mechanisms for fixing a rod 915 in position relative to the spacer 920. With the first wing 930 and the second wing 960 deployed, movement of the implant 900 along the longitudinal axis 925 can be limited or blocked, thereby resisting undesirable displacement of the implant 900.

It should be noted that with implants as described above in reference to FIGS. 22A-23B the rod 915 can optionally be trimmed or otherwise partially detached to decrease a space required to accommodate the implant 900 within the patient's spine. For example, the structure of the rod 915 can be beveled or otherwise weakened near a distal end of the rod 915 to allow the rod 915 to be snapped off when the first and second wings 930,960 are deployed and the rod 915 is fixed in place. In other embodiments, a tool (not shown) can be used to cut the rod 915 after the first and second wings 930,960 are deployed and the rod 915 is fixed in place. Still further, the rod 915 need not comprise a rigid structure, but rather alternatively can include a tether, string, or similarly flexible structure that can be placed in tension to retain the second wing 960 and/or first wing 930 in a deployed position.

Referring to FIGS. 22B, 22C and 23B, the implant 900 is shown having operably connected "hinged" structures 950-957. Such structures can be hinged in any way that permits relative movement. For example, the structures may be hinged by way of flexible straps, for example as described above in reference to FIG. 20B. Alternatively, the structures can be hinged using some other technique. For example, referring to FIG. 24C, one or a pair of cords 996 can connect pairs of hinged structures so that relative movement is restricted, thereby permitting hinging motion, while resisting separation of the structures. In still other embodiments, some other mechanism can be employed to define a range of movement of the hinged structures 950-957. One of ordinary skill in the art will appreciate the myriad different techniques for defining a range of motion of two mechanical parts.

As with the flexible straps 890 above, the cord 996 can be made from a biocompatible material. In an embodiment, the cord 996 can be made from a braided polyester suture material. Braided polyester suture materials include, for example, Ethibond, Ethiflex, Mersilene, and Dacron, and are non-absorbable, having high tensile strength, low tissue reactivity and improved handling. In other embodiments, the cords 996 can be made from stainless steel (i.e., surgical steel), which can be woven into a strap, for example. In still other embodiments, the cords 996 can be made from some other material (or combination of materials) having similar properties.

Materials for Use in Implants of the Present Invention

In some embodiments, the implant can be fabricated from medical grade metals such as titanium, stainless steel, cobalt chrome, and alloys thereof, or other suitable implant material having similar high strength and biocompatible properties. Additionally, the implant can be at least partially fabricated from a shape memory metal, for example Nitinol, which is a combination of titanium and nickel. Such materials are typically radiopaque, and appear during x-ray imaging, and other types of imaging. Implants in accordance with the present invention, and/or portions thereof can also be fabricated from somewhat flexible and/or deflectable material. In these embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers are the polyaryl ester ketones which has several members including polyetheretherketone (PEEK), and polyetherketoneketone (PEKK). PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength. In an embodiment, the implant can be fabricated from PEEK 450G, which is an unfilled PEEK approved for medical implantation available from Victrex. Other sources of this material include Gharda located in Panoli, India. PEEK 450G has the following approximate properties:

| Property | Value |
| --- | --- |
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

PEEK 450G has appropriate physical and mechanical properties and is suitable for carrying and spreading a physical load between the adjacent spinous processes. The implant and/or portions thereof can be formed by extrusion, injection, compression molding and/or machining techniques.

It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketoneketone (PEKEKK), polyetheretherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

As described above, the binder can be made from a biocompatible material. In an embodiment, the binder can be made from a braided polyester suture material. Braided polyester suture materials include, for example, Ethibond, Ethiflex, Mersilene, and Dacron, and are nonabsorbable, having high tensile strength, low tissue reactivity and improved handling. In other embodiments, the binder can be made from stainless steel (i.e., surgical steel), which can be braided into a tether or woven into a strap, for example. In still other embodiments, the binder can be made from some other material (or combination of materials) having similar properties.

Figure 24:
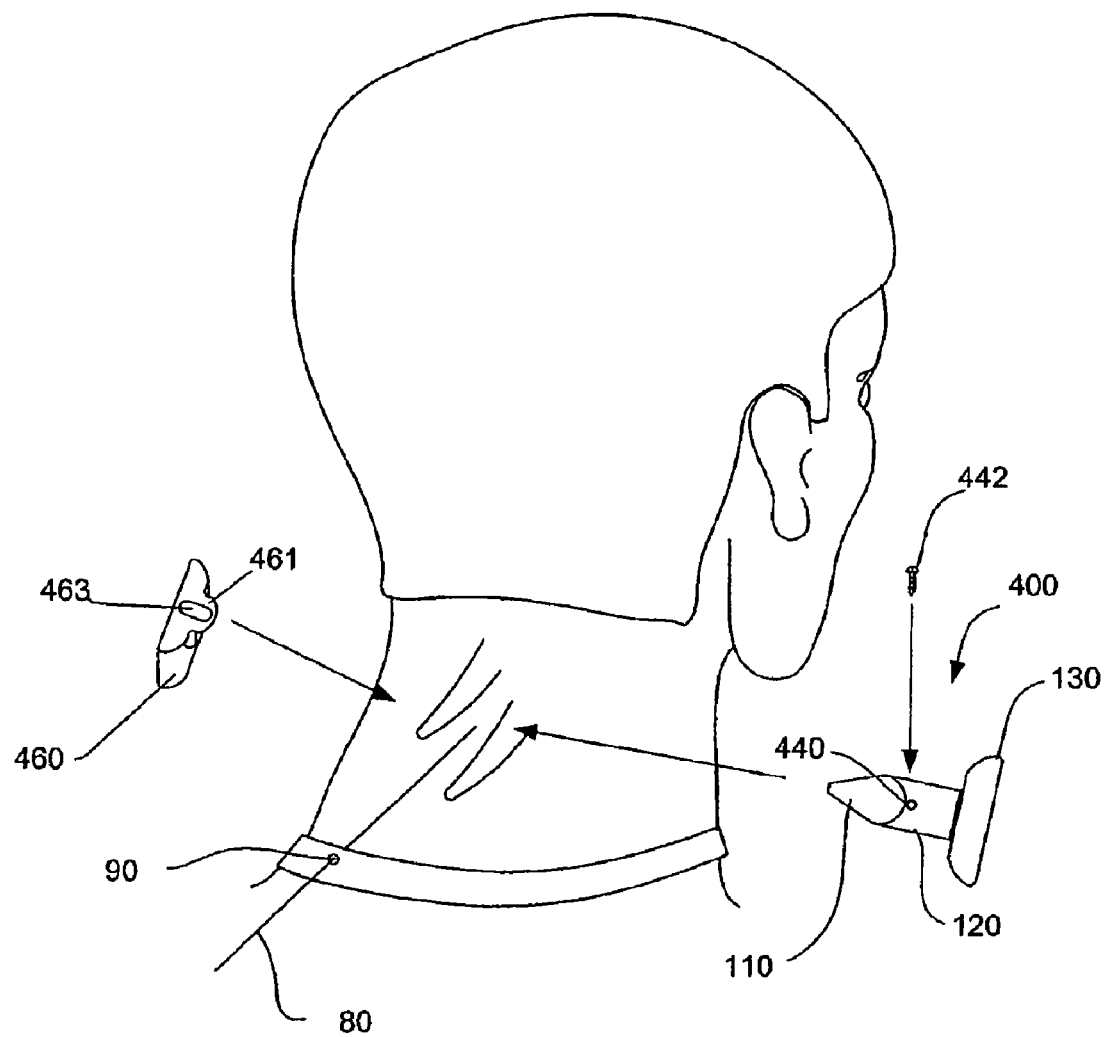
FIG. 24 illustrates an embodiment of a method for implanting an interspinous implant as shown in FIGS. 1-17 in accordance with the present invention.

It is to be understood that embodiments in accordance with the present invention can be constructed without a pliant material. It is also to be understood that the embodiments in accordance with the present invention can have other dimensions Methods for implanting Interspinous Implants A minimally invasive surgical method for implanting an implant 400 in the cervical spine is disclosed and taught herein. In this method, as shown in FIG. 24, preferably a guide wire 80 is inserted through a placement network or guide 90 into the neck of the implant recipient. The guide wire 80 is used to locate where the implant is to be placed relative to the cervical spine, including the spinous processes. Once the guide wire 80 is positioned with the aid of imaging techniques, an incision is made on the side of the neck so that an implant in accordance with an embodiment of the present invention, can be positioned in the neck thorough an incision and along a line that is about perpendicular to the guide wire 80 and directed at the end of the guide wire 80. In one embodiment, the implant can be a sized implant 400 (i.e., having a body that is not distractable), such as described above in FIGS. 1-17 and including a distraction guide 110, a spacer 120, and a first wing 130. The implant 400 is inserted into the neck of the patient. Preferably during insertion, the distraction guide 110 pierces or separates the tissue without severing the tissue.

Once the implant 400 is satisfactorily positioned, a second wing 460 can be optionally inserted along a line that is generally colinear with the line over which the implant 400 is inserted but from the opposite side of the neck. The anatomy of the neck is such that it is most convenient and minimally invasive to enter the neck from the side with respect to the implant 400 and the second wing 460. The second wing 460 is mated to the implant and in this particular embodiment, the second wing 460 is attached to the implant 400 by the use of a fastener, for example by a screw 442. Where a screw is used, the screw 442 can be positioned using a screw driving mechanism that is directed along a posterior to anterior line somewhat parallel to the guide wire 80. This posterior to anterior line aids the physician in viewing and securing the second wing 460 to the implant. The second wing 460 is positioned so that a bore 463 formed in a lip 461 of the second wing 460 is aligned with a bore 440 of the implant 400, as described above. The screw 442 is positioned within both bores and secured, at least, to the bore 440 of the implant 400. In other embodiments, the second wing can be interference fit with the implant, as described above, or fastened using some other mechanism, such as a flexible hinge and protrusion.

Figure 25:
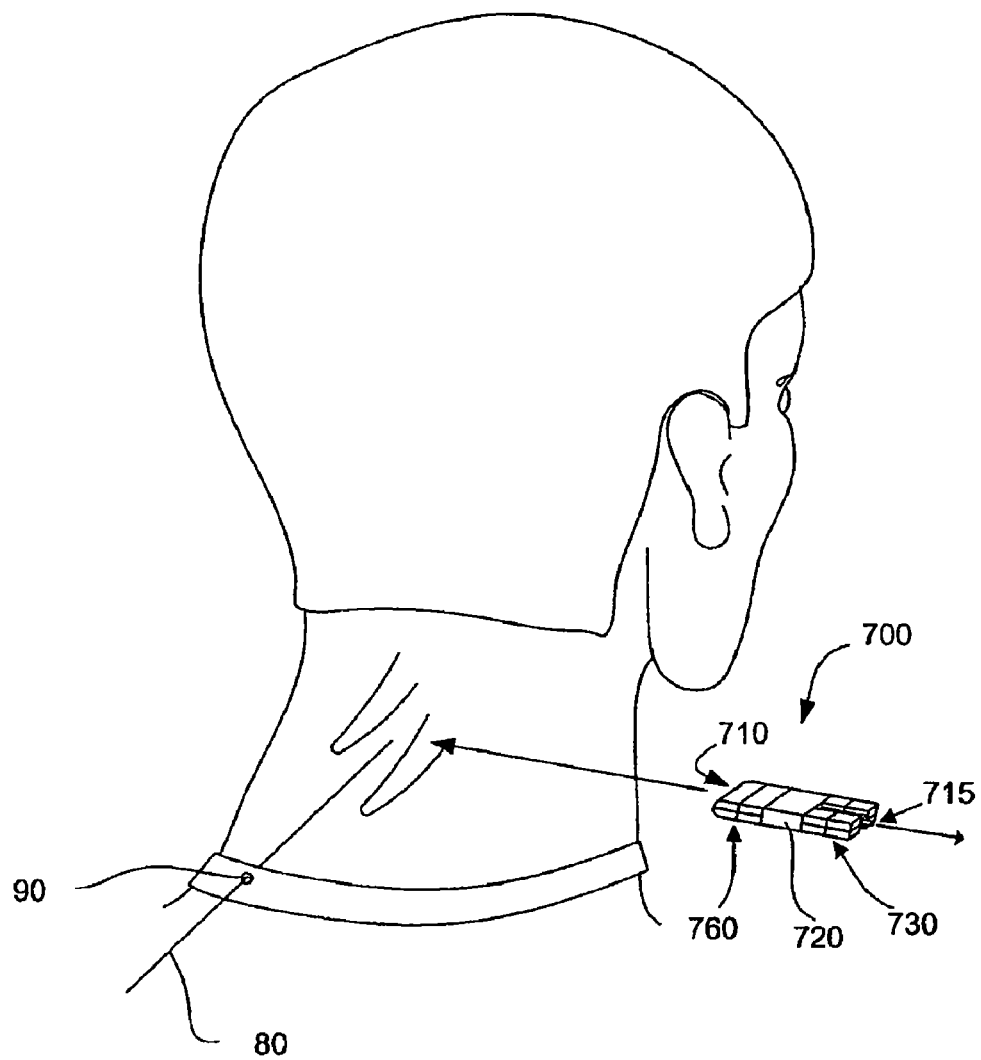
FIG. 25 illustrates an embodiment of a method for implanting an interspinous implant as shown in FIGS. 18A-21 having deployable first and second wings in accordance with the present invention.

A minimally invasive surgical method for implanting an alternative embodiment of an implant 700 in the cervical spine is disclosed and taught herein. In this method, as shown in FIG. 25, preferably a guide wire 80 is inserted through a placement network or guide 90 into the neck of the implant recipient. The guide wire 80 is used to locate where the implant 700 is to be placed relative to the cervical spine, including the spinous processes. Once the guide wire 80 is positioned with the aid of imaging techniques, an incision is made on the side of the neck so that an implant 700 in accordance with an embodiment of the present invention, can be positioned in the neck thorough an incision and along a line that is about perpendicular to the guide wire 80 and directed at the end of the guide wire 80. In an embodiment, the implant 700 can include a distraction guide 710, a spacer 720, a rod 715 extending through the spacer 720, and deployable first and second wings 730,760. The implant 700 can have a substantially flat profile to ease implantation, as described above. The implant 700 is inserted into the neck of the patient. Preferably during insertion, the distraction guide 710 pierces or separates the tissue without severing the tissue.

Once the implant 700 is satisfactorily positioned, the first wing 730 and the second wing 760 can be deployed. As described above, the second wing 760 can be deployed by urging the rod 715 in a direction opposite the direction of insertion along the longitudinal axis 725. As the rod 715 travels through the spacer 720, hinged structures 750-753 contact the spacer 720, buckle and extend away from the rod 715 two form an upper end 762 of the second wing and a lower end 764 of the second wing. When second wing 760 is satisfactorily deployed, the rod 715 can be fixed in place relative to the spacer 720 using a first stop 782, a pin, or some other mechanism. The first wing 730 can be deployed by urging the hinged structures 754-757 toward the spacer 720, causing the hinged structures 754-757 to buckle and extend away from one another to form an upper end 732 of the second wing and a lower end 734 of the second wing. The anatomy of the neck is such that it is most convenient and minimally invasive to enter the neck from the side with respect to the implant 700.

Figure 26:
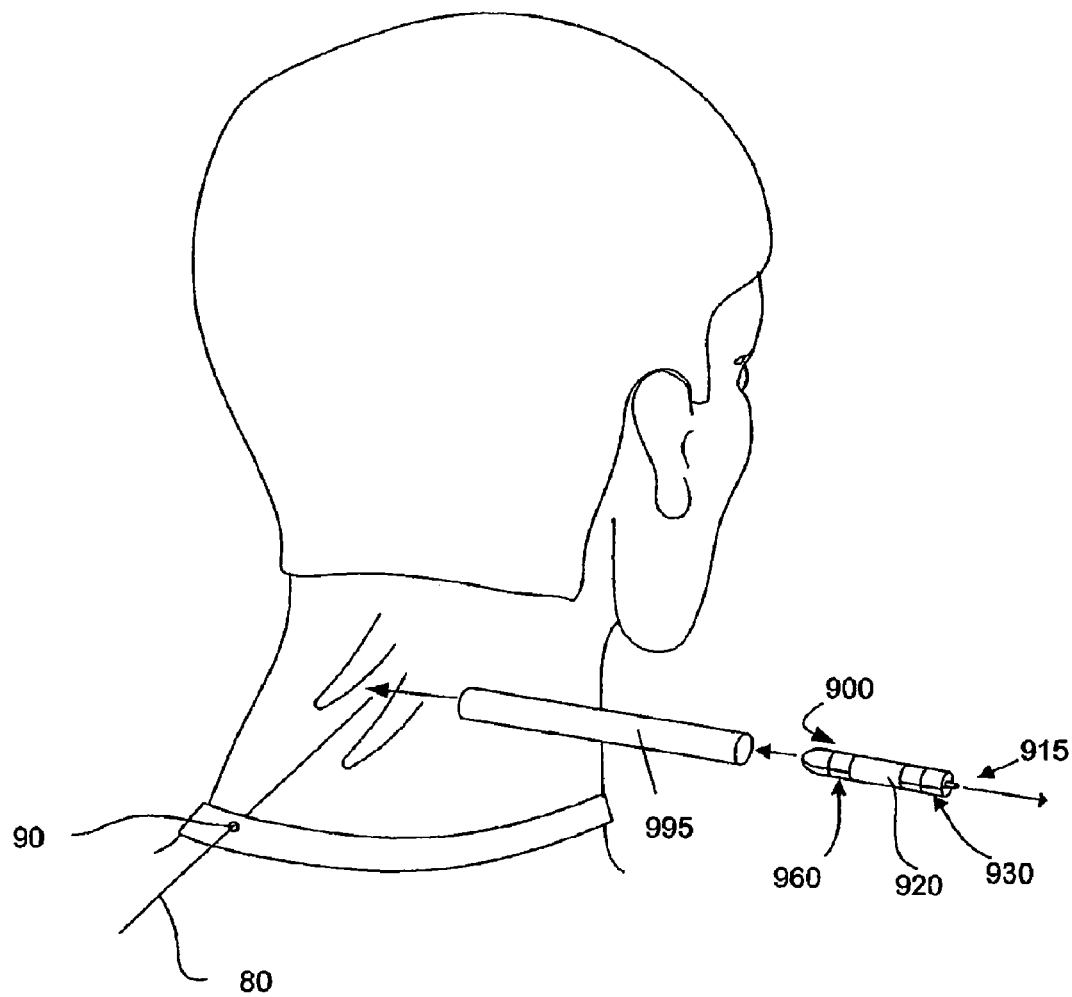
FIG. 26 illustrates an alternative embodiment of a method for implanting an interspinous implant as shown in FIGS. 22A-23B having deployable first and second wings by way of a cannula inserted between adjacent spinous processes in accordance with the present invention.

A minimally invasive surgical method for implanting an alternative embodiment of an implant 900 in the cervical spine is disclosed and taught herein. In this method, as shown in FIG. 26, preferably a guide wire 80 is inserted through a placement network or guide 90 into the neck of the implant recipient. The guide wire 80 is used to locate where the implant 900 is to be placed relative to the cervical spine, including the spinous processes. Once the guide wire 80 is positioned with the aid of imaging techniques, an incision is made on the side of the neck along a line that is about perpendicular to the guide wire 80 and directed at the end of the guide wire 80. The cannula 995 is fed through the incision and positioned between the targeted adjacent spinous processes. In an embodiment, the implant 900 can include a distraction guide 910, a spacer 920, a rod 915 extending through the spacer 920, and deployable first and second wings 930,960. The implant 900 can have a substantially circular cross-section to roughly conform with an inside surface of the cannula 995. The implant 900 is urged through the cannula 995 and into position between the adjacent spinous processes so that the second wing 960 hinge structures are clear of the cannula 995, as described above in reference to FIG. 23B. The second wing 960 is then deployed by urging the rod 915 in a direction opposite the direction of insertion along the longitudinal axis 925. As the rod 915 travels through the spacer 920, hinged structures 950-953 contact the spacer 920, buckle and extend away from the rod 915 two form an upper end 962 of the second wing and a lower end 964 of the second wing. When second wing 960 is satisfactorily deployed, the cannula 995 can be retracted to expose the hinged structures 954-957 of the first wing 930. The first wing 930 can be deployed by urging the hinged structures 954-957 toward the spacer 920, causing the hinged structures 954-957 to buckle and extend away from one another to form an upper end 932 of the second wing and a lower end 934 of the second wing. Once the first wing 930 is deployed, the rod 915 can optionally be shortened, and the cannula 995 can be withdrawn from the incision. The incision can then be closed.

The foregoing description of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. An apparatus, comprising:
   an interspinous-process spacer having a first expandable wing, a second expandable wing, a body disposed between the first and second expandable wings, and an inner elongate member; the spacer further comprising a longitudinal axis; a proximal direction defined along the axis from the first wing toward the second wing;
   the first and second expandable wings movable from collapsed configuration to an expanded configuration; the first and second expandable wings extending relatively further from the axis in their expanded configurations than in their collapsed configurations;
   the inner elongate member having a complimentary fit within a lumen defined by the expandable wing when the expandable wing is in a collapsed configuration;
   the elongate member being non-hollow and having a portion thereof that is disposed proximally relative to the body and overlapped by the second wing when the first and second wings are in their collapsed configurations;
   wherein the elongate member is longitudinally displaceable proximally relative to the body to cause both:
   the first and second wings to move from their collapsed configurations to their expanded configurations;
   the portion of the elongate member to be disposed more proximally than the second wing so that the second wing is disposed between the portion of the elongate member and the body.

2. The apparatus of claim 1 wherein the first expandable wing includes a portion having an inner diameter substantially corresponding to the outer diameter of the inner elongate member.

3. The apparatus of claim 1 wherein the first expandable wing includes a first portion and a second portion different from the first portion, the first portion having an inner diameter substantially corresponding to the outer diameter of the inner elongate member, the second portion of the expandable wing being substantially planar.

4. The apparatus of claim 1 wherein:
   the first expandable wing includes a distal portion and a proximal portion different from the distal portion,
   a planar portion of the distal portion being substantially parallel with a planar portion of the proximal portion when the expandable wing is in the collapsed configuration,
   the planar portion of the distal portion being non-parallel to the planar portion of the proximal portion when the expandable wing is in an expandable configuration.

5. The apparatus of claim 1 wherein the first expandable wing includes an upper portion and a lower portion, the upper portion and the lower portion collectively defining the lumen of the expandable wing when the expandable wing is in the collapsed configuration.

6. The apparatus of claim 1 wherein the first expandable wing includes an upper portion and a lower portion, the upper portion having a planar portion substantially parallel with a planar portion of the lower portion when the expandable wing is in the collapsed configuration.

7. The apparatus of claim 1 wherein the first expandable wing includes an upper portion and a lower portion, the upper portion having a first planar portion and a second portion each being non-parallel with a first planar portion and a second planar portion of the lower portion when the expandable wing is in an expandable configuration.

8. The apparatus of claim 1 wherein a distal end of the first expandable wing is configured to distract a space between a pair of adjacent spinous processes when the interspinous-process spacer is inserted between the pair of adjacent spinous processes and the expandable wing is in a collapsed configuration.

9. The apparatus of claim 1 wherein the elongate member is a rigid rod.

* * * * *